United States Patent
Sarathy et al.

(10) Patent No.: US 10,947,129 B2
(45) Date of Patent: Mar. 16, 2021

(54) FLUID DISINFECTION WITH ULTRAVIOLET RADIATION AND A CHEMICAL DISINFECTANT

(71) Applicant: Trojan Technologies, London (CA)

(72) Inventors: Siva Rajan Sarathy, London (CA); Adrian Harrison Murray, London (CA); Domenico Santoro, London (CA); John Walton, Colfax, CA (US); Paris Neofotistos, Midlothian, VA (US); Yuri Lawryshyn, Midhurst (CA)

(73) Assignee: TROJAN TECHNOLOGIES GROUP ULC, London (CA)

( * ) Notice: Subject to any disclaimer, the term of this patent is extended or adjusted under 35 U.S.C. 154(b) by 268 days.

(21) Appl. No.: 15/753,940

(22) PCT Filed: Aug. 22, 2016

(86) PCT No.: PCT/CA2016/050982
§ 371 (c)(1),
(2) Date: Feb. 20, 2018

(87) PCT Pub. No.: WO2017/027982
PCT Pub. Date: Feb. 23, 2017

(65) Prior Publication Data
US 2018/0265375 A1 Sep. 20, 2018

Related U.S. Application Data

(60) Provisional application No. 62/207,734, filed on Aug. 20, 2015.

(51) Int. Cl.
*C02F 1/00* (2006.01)
*C02F 1/32* (2006.01)
(Continued)

(52) U.S. Cl.
CPC ............. *C02F 1/008* (2013.01); *A61L 2/10* (2013.01); *A61L 2/18* (2013.01); *A61L 2/186* (2013.01);
(Continued)

(58) Field of Classification Search
CPC ...... C02F 1/00; C02F 1/32; C02F 1/72; C02F 1/008; C02F 1/722; C02F 1/76;
(Continued)

(56) References Cited

U.S. PATENT DOCUMENTS

2005/0021808 A1 10/2005 Williamson et al.
2013/0098844 A1* 4/2013 Forstmeier .............. C02F 1/008
                                                        210/739
(Continued)

FOREIGN PATENT DOCUMENTS

WO    WO-2012171758 A1 * 12/2012 ............... C02F 1/32
WO    WO2012171758 A1    12/2012
WO    2016/205944        12/2016

OTHER PUBLICATIONS

European Patent Office, Supplementary European Search Report, dated Jun. 26, 2018, pp. 4, dated Jun. 26, 2018.
(Continued)

*Primary Examiner* — Robert Clemente
*Assistant Examiner* — Akash K Varma
(74) *Attorney, Agent, or Firm* — Ference & Associates LLC

(57) ABSTRACT

There is described an on-line device for controlling a fluid treatment process configured to inactivate a microorganism in a flow of fluid using ultraviolet radiation and a chemical disinfectant. The device includes: a memory for receiving a calculated database of dose response for the ultraviolet radiation and for the chemical disinfectant for a fluid treatment parameter; means to obtain input data about the fluid (Continued)

First example of method for sizing and selection of combined UV and peracid disinfection process.

treatment parameter from the process; means to compare the input data with calculated database; and means to adjust one or more of the amount ultraviolet radiation and the chemical disinfectant added to the flow fluid in response to a difference between the input data and calculated database. There is also described a process for controlling a fluid treatment process configured to inactivate a microorganism in a flow of fluid using ultraviolet radiation and a chemical disinfectant.

16 Claims, 25 Drawing Sheets

(51) Int. Cl.
  C02F 1/72    (2006.01)
  A61L 2/10    (2006.01)
  A61L 2/18    (2006.01)
  A61L 2/24    (2006.01)
  C02F 1/76    (2006.01)
  C02F 1/78    (2006.01)
(52) U.S. Cl.
  CPC .............. *A61L 2/24* (2013.01); *C02F 1/32* (2013.01); *C02F 1/722* (2013.01); *C02F 1/76* (2013.01); *C02F 1/78* (2013.01); *C02F 2201/326* (2013.01); *C02F 2209/006* (2013.01); *C02F 2209/02* (2013.01); *C02F 2209/40* (2013.01); *C02F 2303/04* (2013.01)

(58) Field of Classification Search
  CPC .. C02F 1/78; C02F 2303/04; C02F 2209/006; C02F 2209/02; C02F 2209/40; C02F 2201/326; A61L 2/10; A61L 2/18; A61L 2/186; A61L 2/24
  USPC ........................................................ 210/739
  See application file for complete search history.

(56) References Cited

U.S. PATENT DOCUMENTS

2013/0220941 A1* 8/2013 Kekko ................... C02F 1/68
                                                     210/748.1
2014/0373926 A1* 12/2014 Jha ..................... G01M 99/005
                                                     137/2

OTHER PUBLICATIONS

Beber De Souza, Jeanette, et al., "Water and Wastewater Disinfection with Peracetic Acid and UV Radiation and Using Advanced Oxidative Process PAA/UV", International Journal of Photoenergy, vol. 2015, Jan. 1, 2015 (Jan. 1, 2015), pp. 1-7, XP055487852, US ISSN: 1110-662X~ DOI, 10.1155/2015/860845, 1/1/5.
Canadian Intellectual Property Office, International Search Report, dated Dec. 5, 2016, 1 page, Canadian Intellectual Property Office, Gatineau, Quebec, Canada.

* cited by examiner

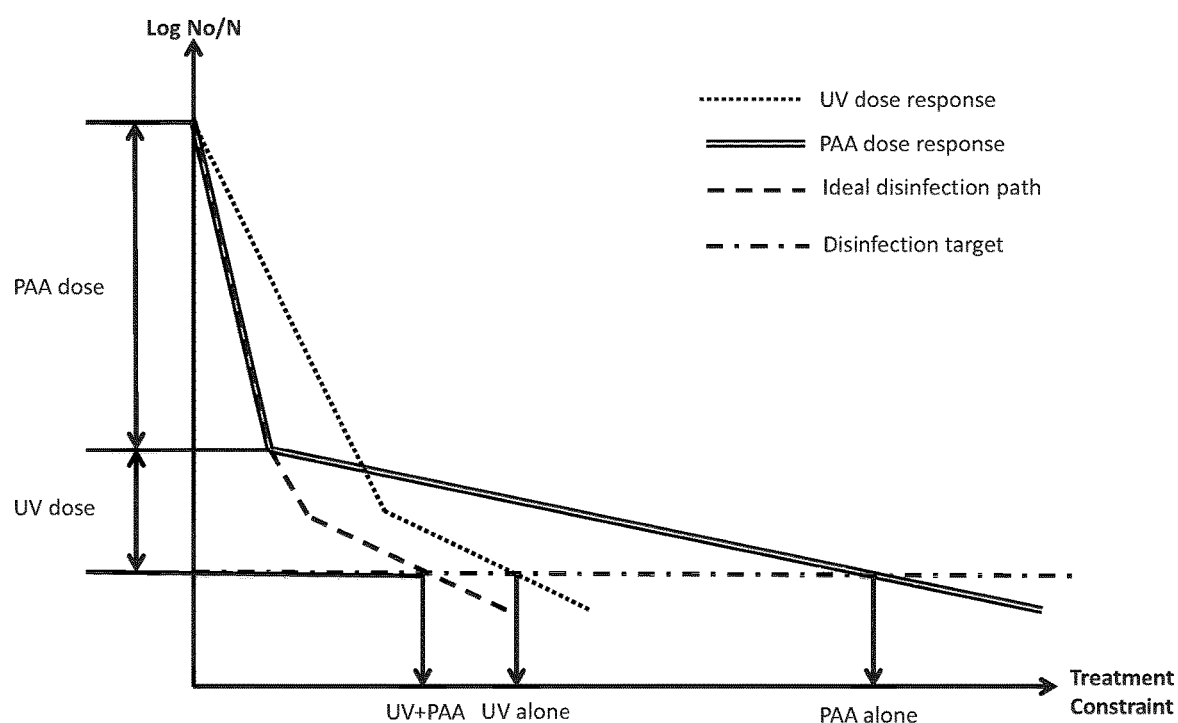
Figure 1: First example of method for sizing and selection of combined UV and peracid disinfection process.

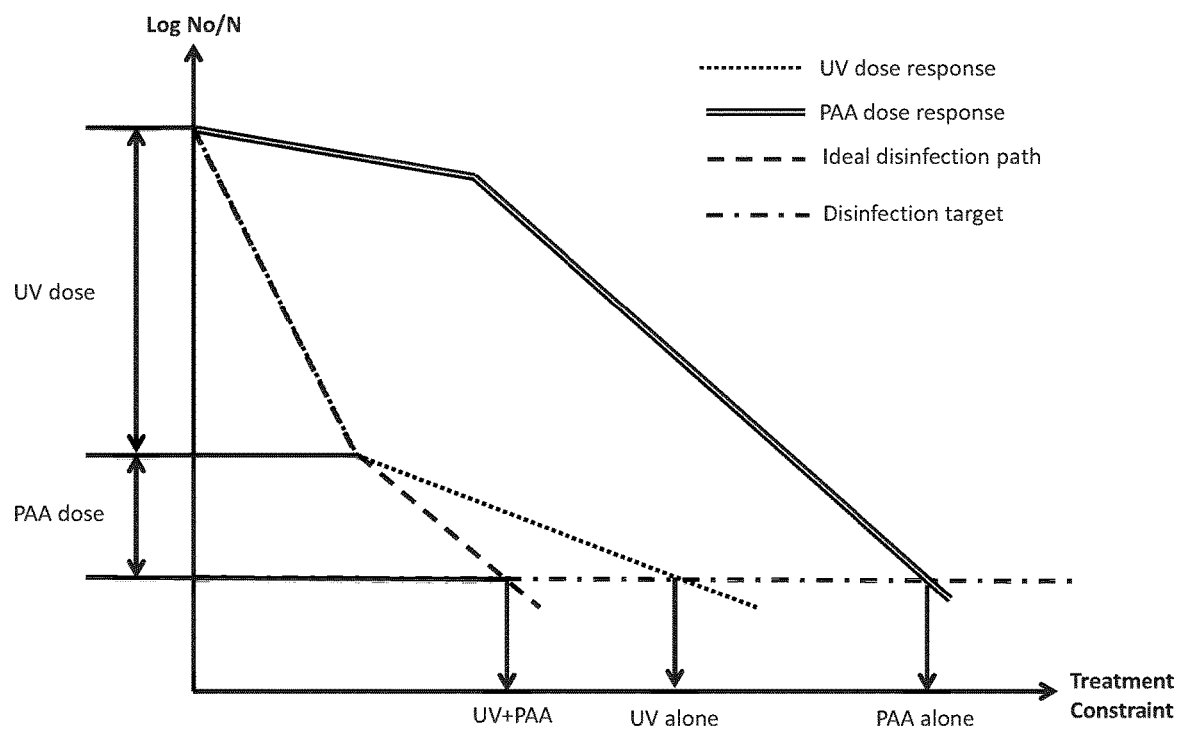
Figure 2: Second example of method for sizing and selection of combined UV and peracid disinfection process.

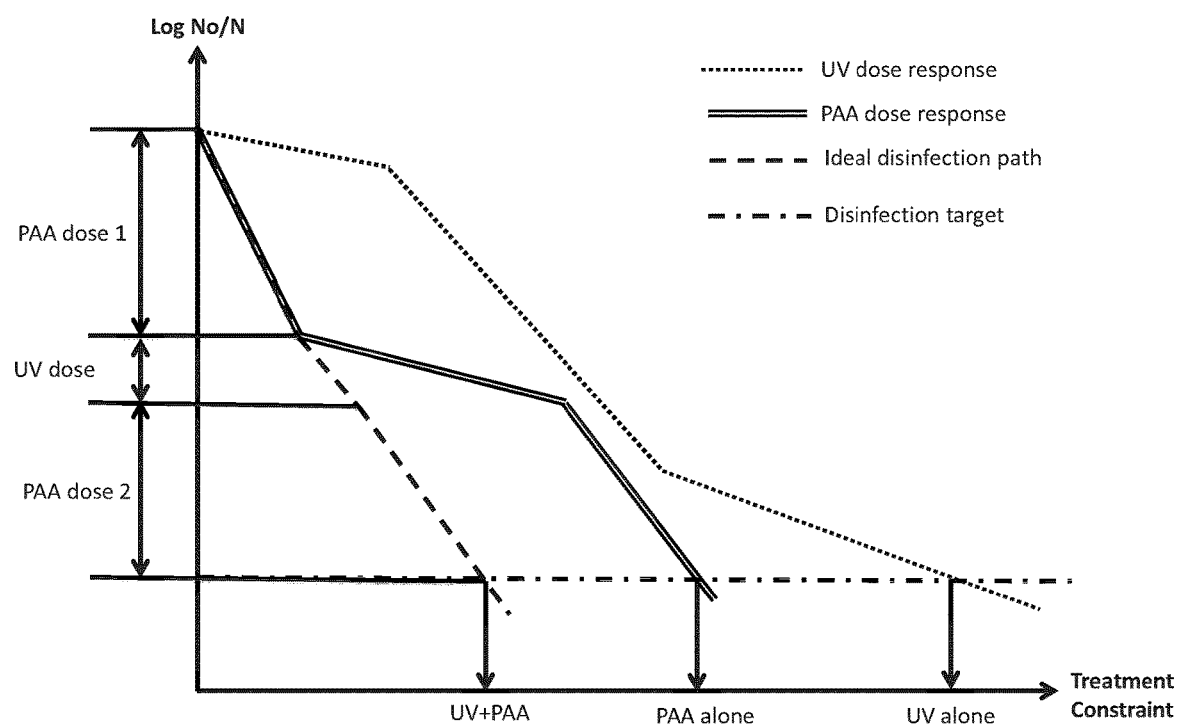
Figure 3: Third example of method for sizing and selection of combined UV and peracid disinfection process.

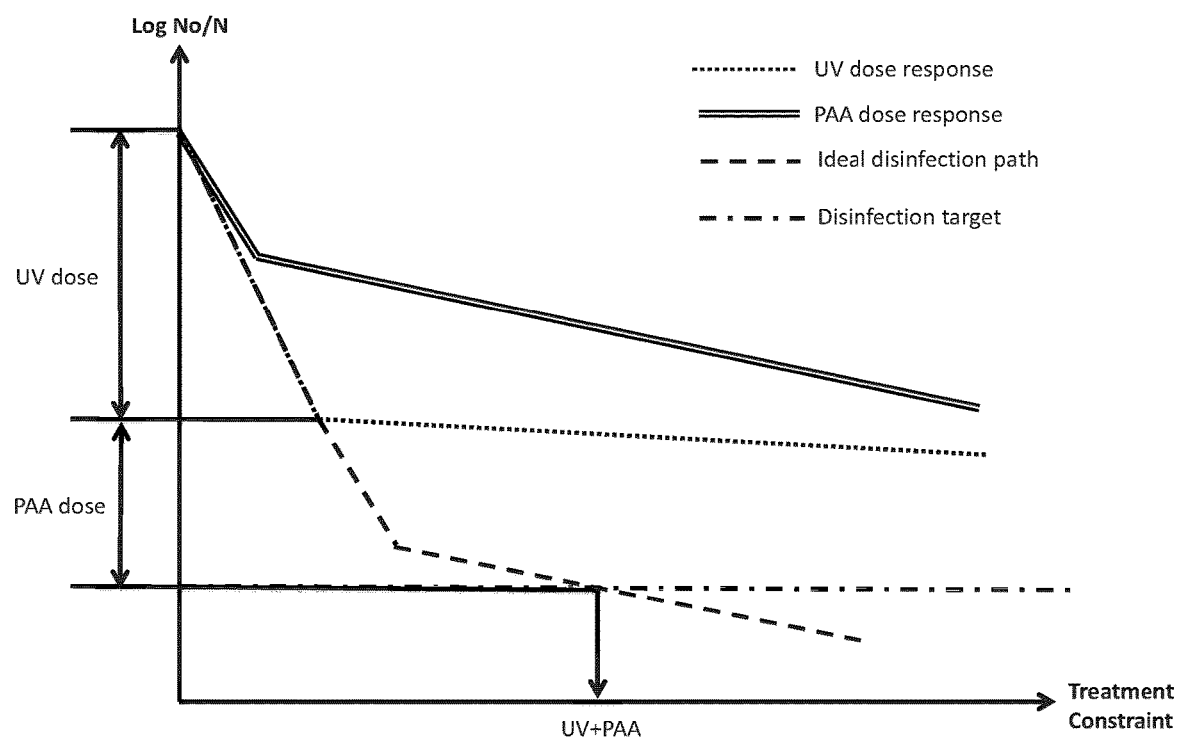
Figure 4: Fourth example of method for sizing and selection of combined UV and peracid disinfection process.

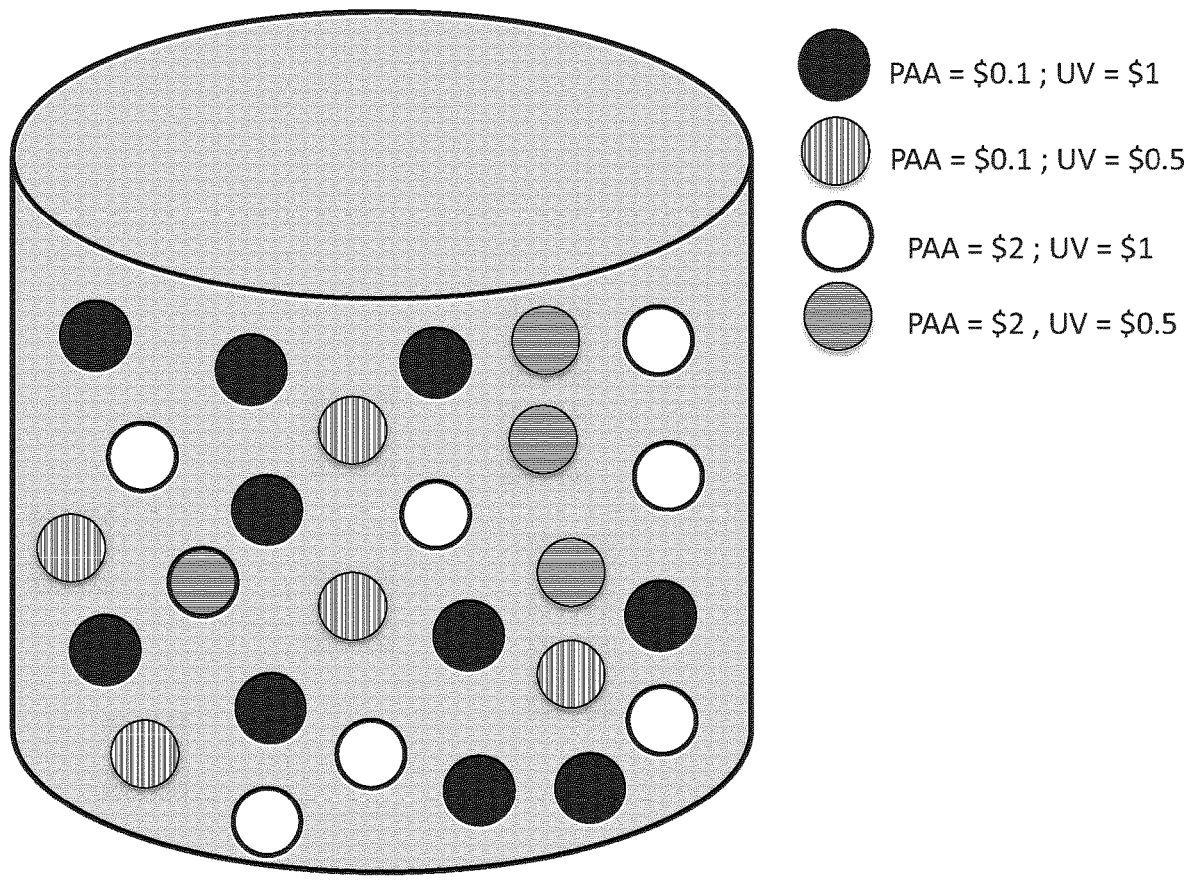
Figure 5: A bucket of water microorganims consisting of four different populations of microganisms with varying resistance to UV or PAA.

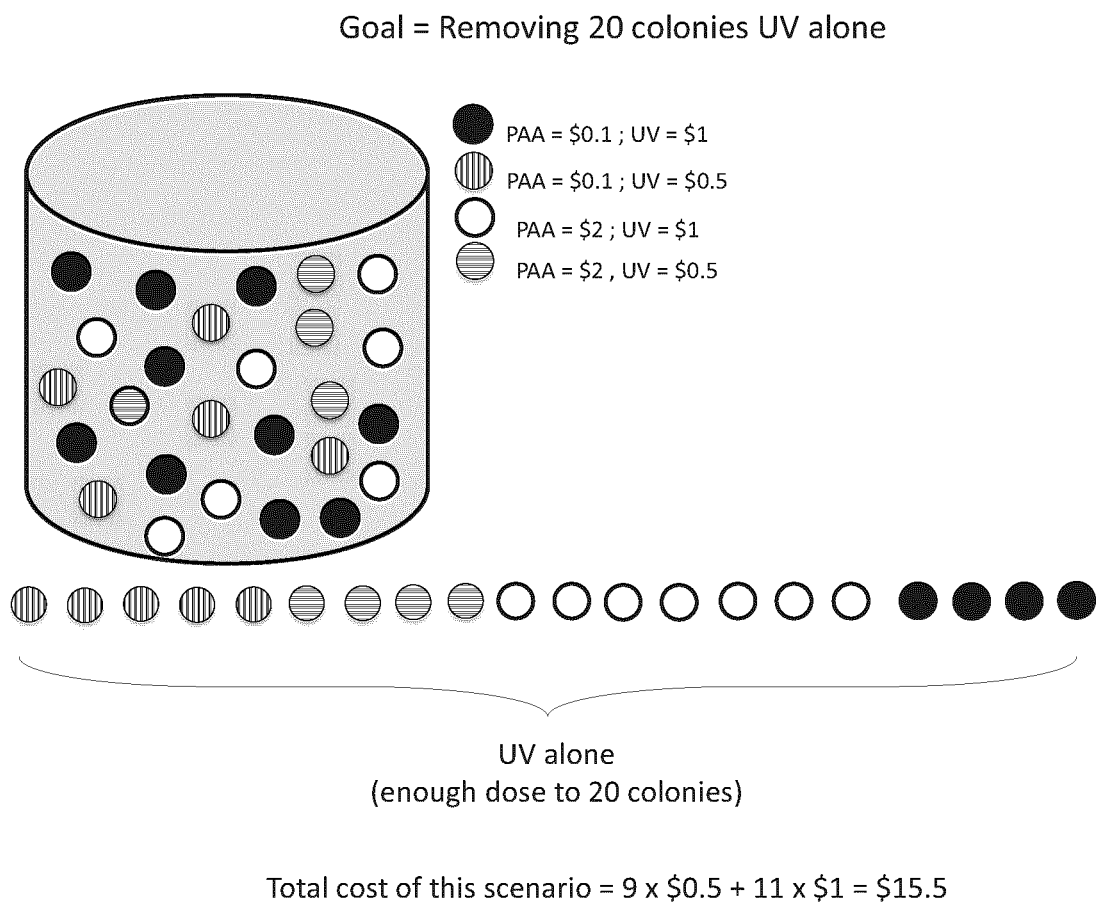
Figure 6: Illustration of cost associated with removing 20 colonies by UV alone

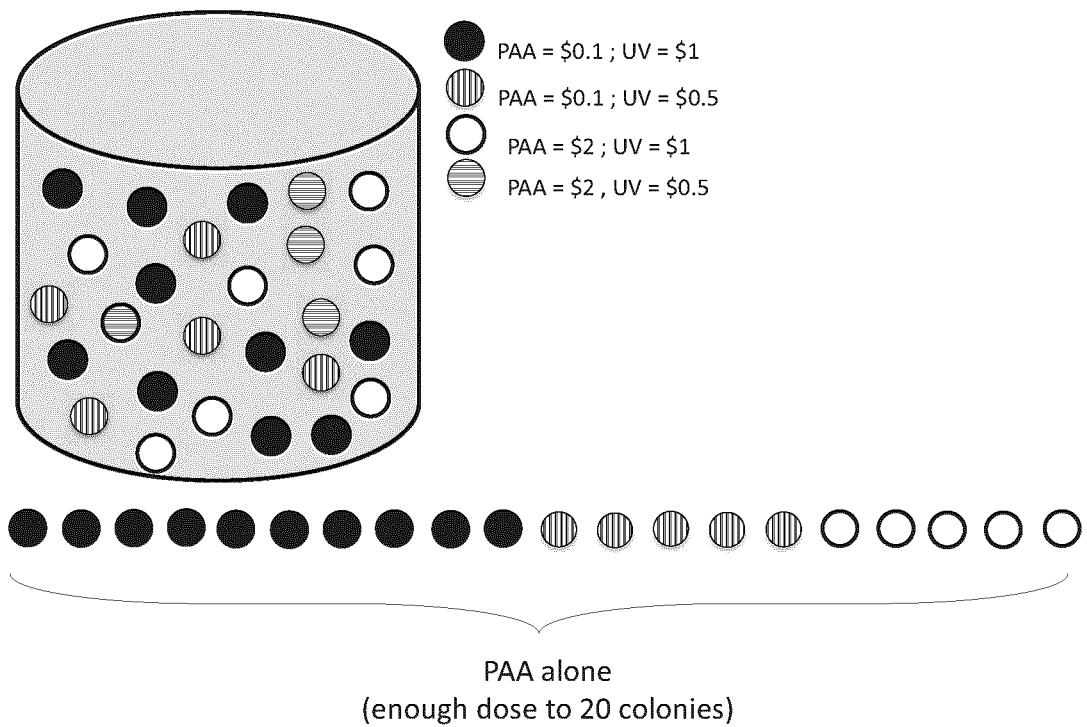
Figure 7: Illustration of cost associated with removing 20 colonies by PAA alone

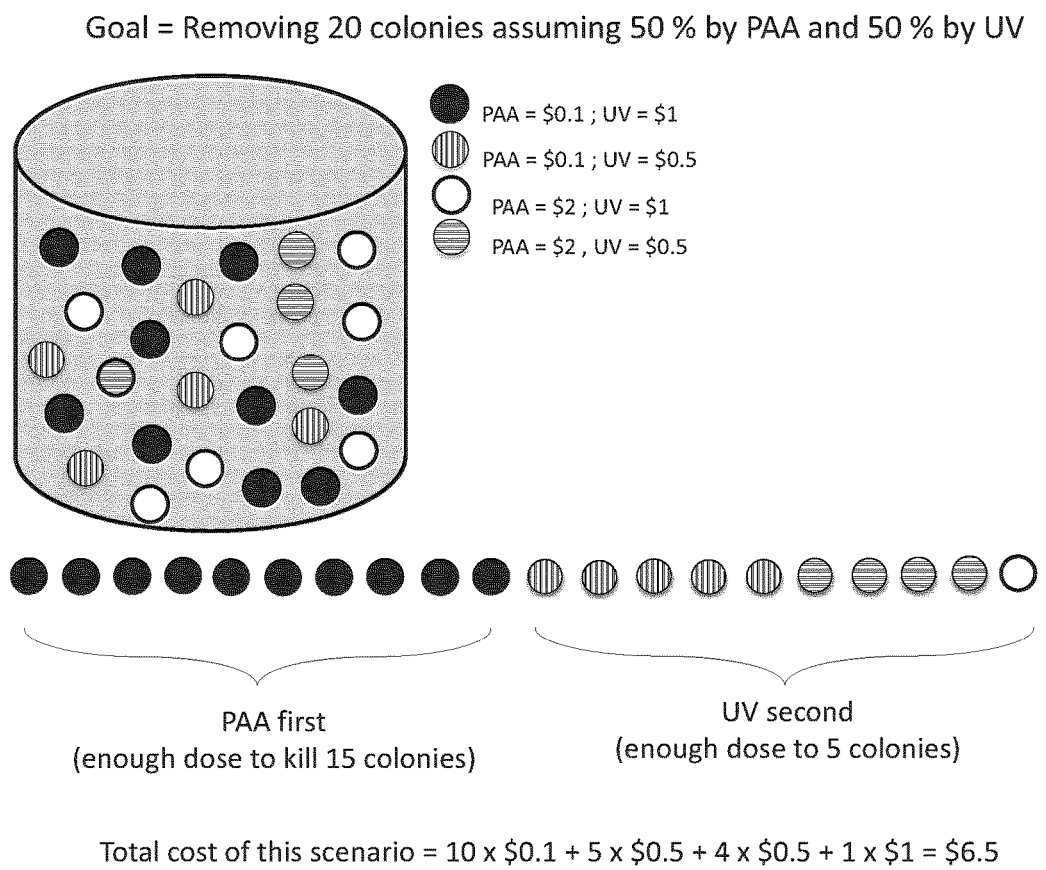
Figure 8: Illustration of cost associated with removing 20 colonies by 50% PAA and 50% UV.

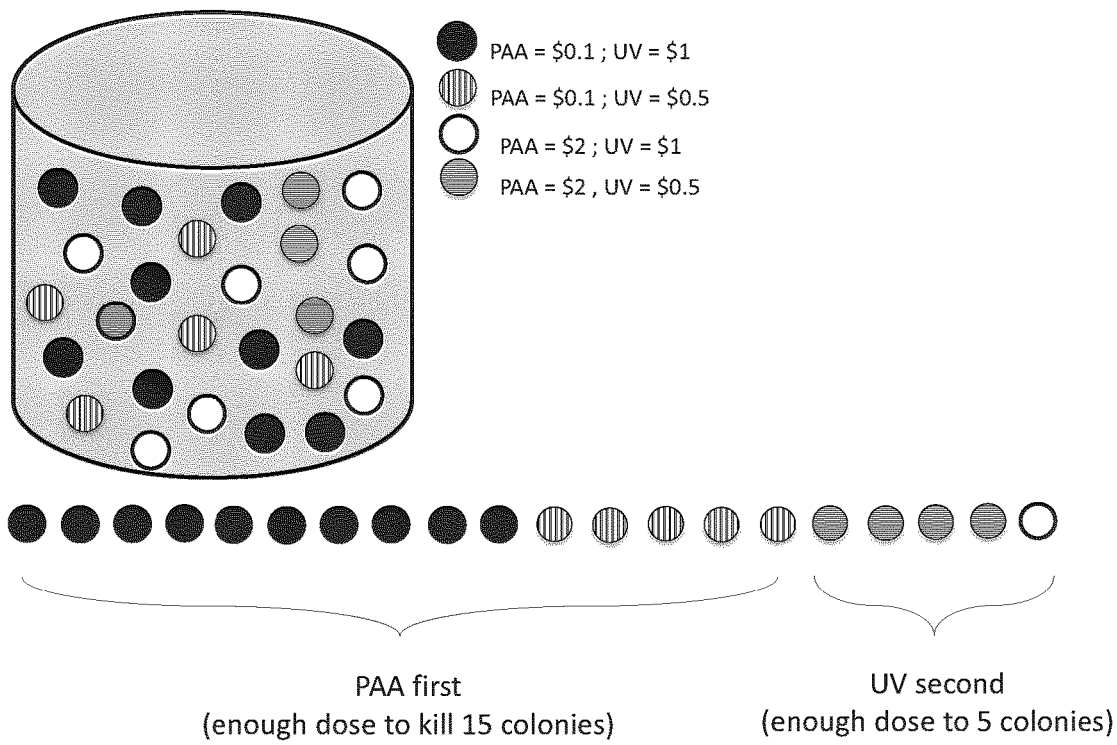
Figure 9: Illustration of cost associated with removing 20 colonies using our optimized algorithm.

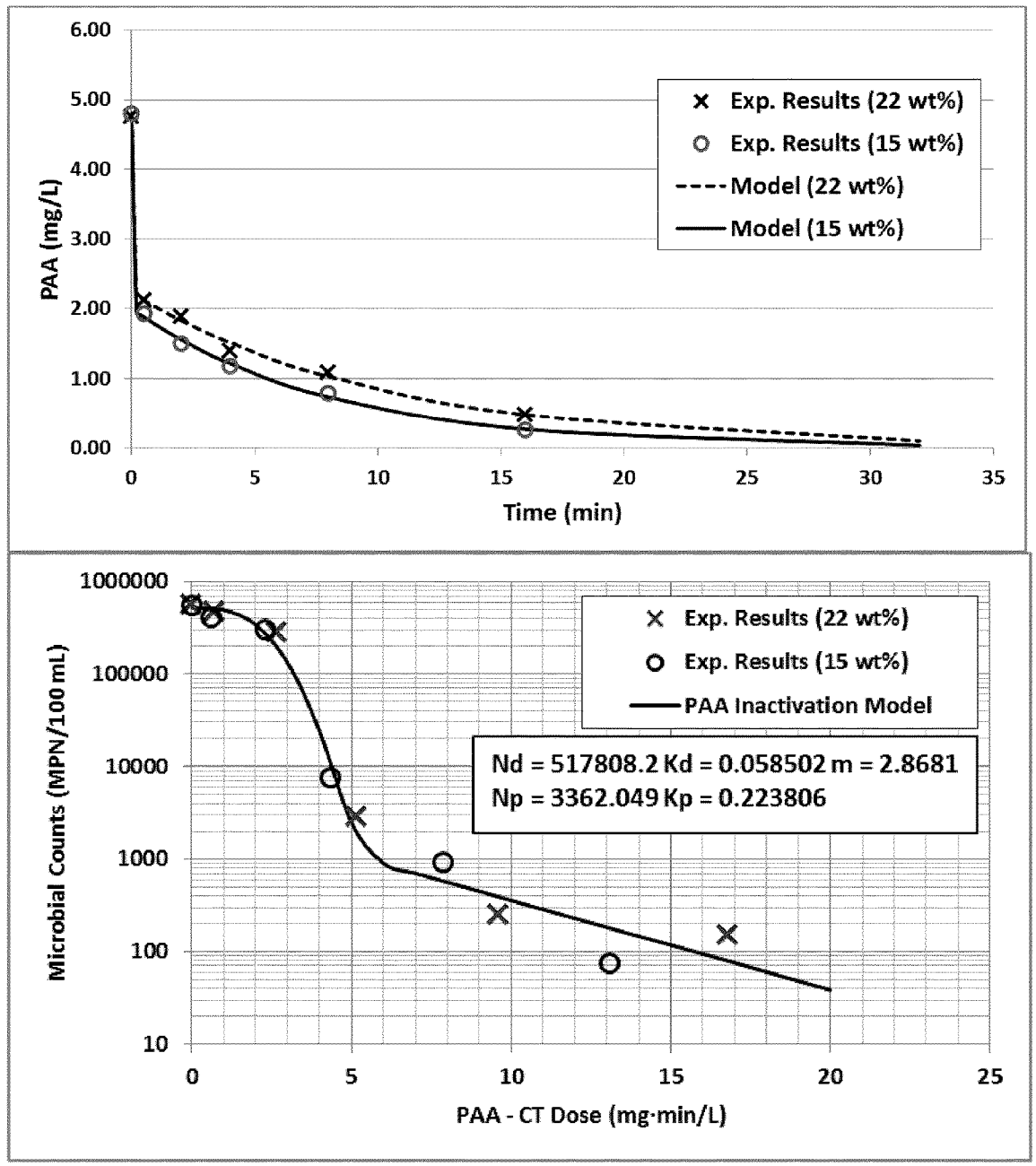
Figure 10: PAA demand/decay for 22% and 15% PAA solutions added to WWTP Secondary Effluent at $C_O$ = 5 mg/L (Top) Data modeled (black lines) from experimental results using Equation 1. Microbial inactivation of WWTP Secondary Effluent treated with 22% and 15% PAA solutions at a CO = 5 mg/L (Bottom)

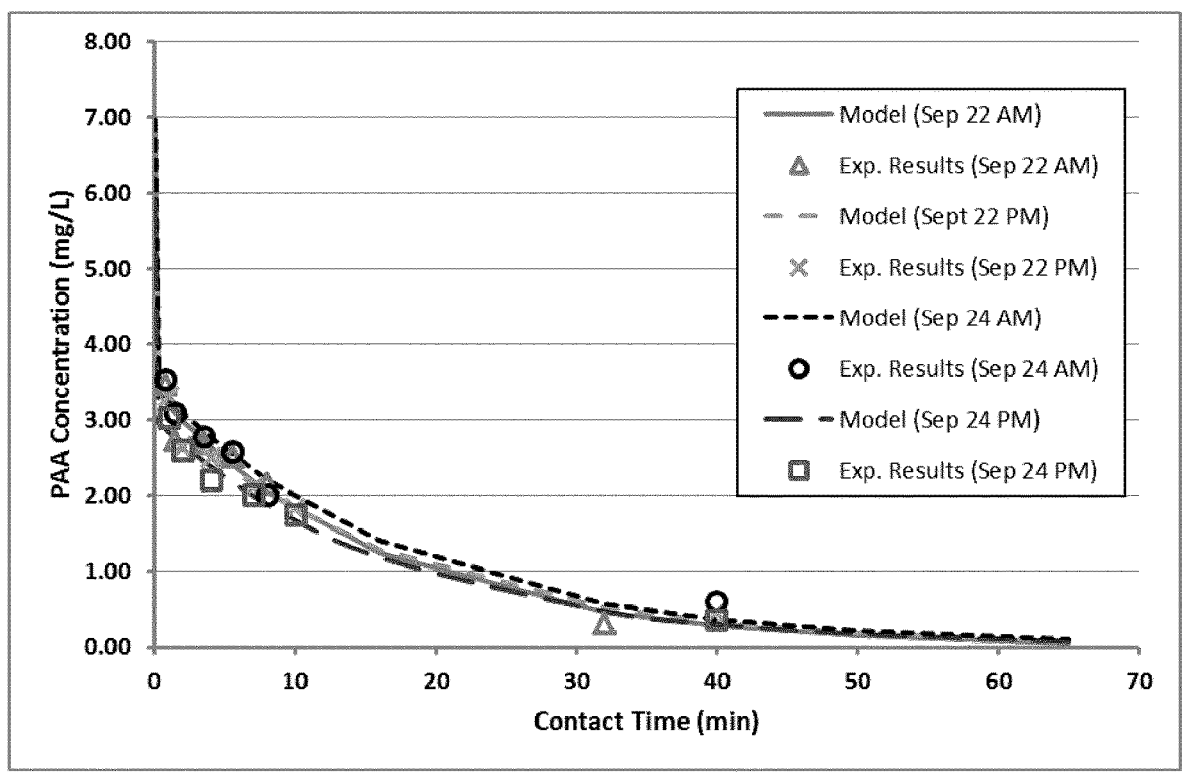
Figure 11: PAA demand/decay model plots for Samples collected Sept 22 and Sept 24 (model curves generated from experimental results using Equation 1).

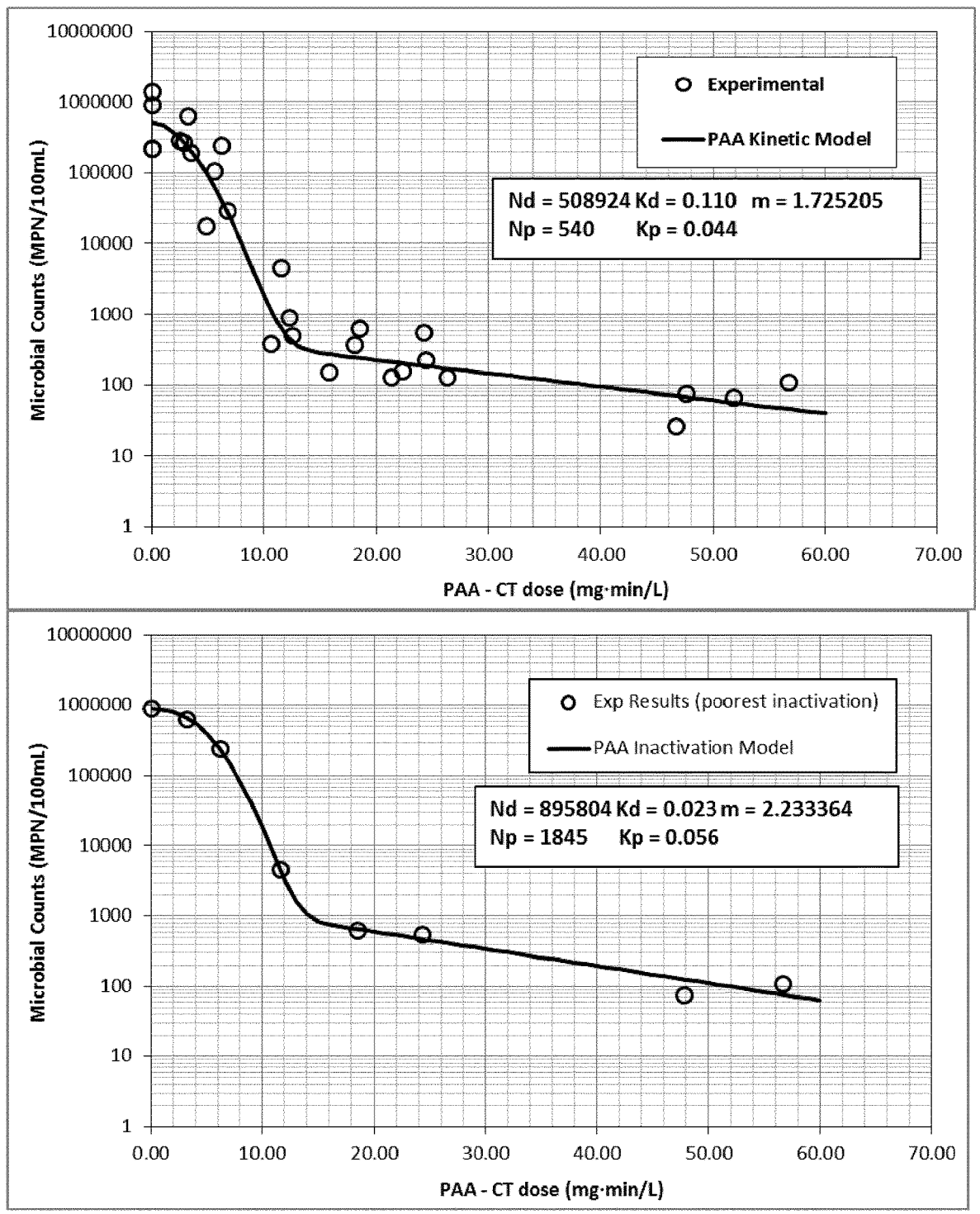
Figure 12: The inactivation of *E. coli* using PAA for WWTP Secondary Effluent samples collected Sept. 22 and Sept. 24 (Top). Inactivation curve for poorest inactivation levels measured on Sept. 22 and Sept. 24 (Bottom).

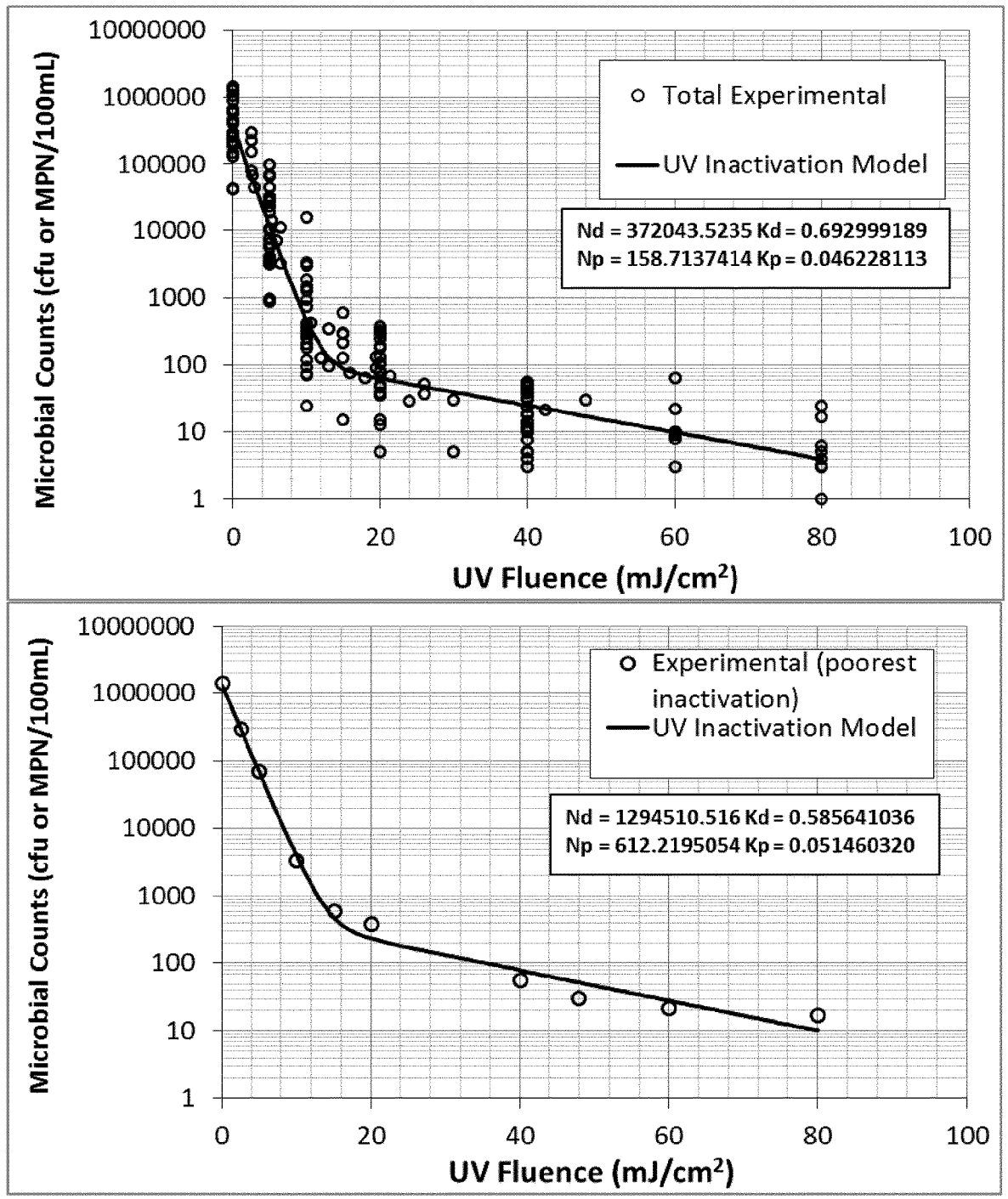
Figure 13: Inactivation of *E. coli* using UV for WWTP Secondary Effluent samples collected 2013 and 2015. Inactivation curves for all data points (top) and poorest inactivation levels (bottom).

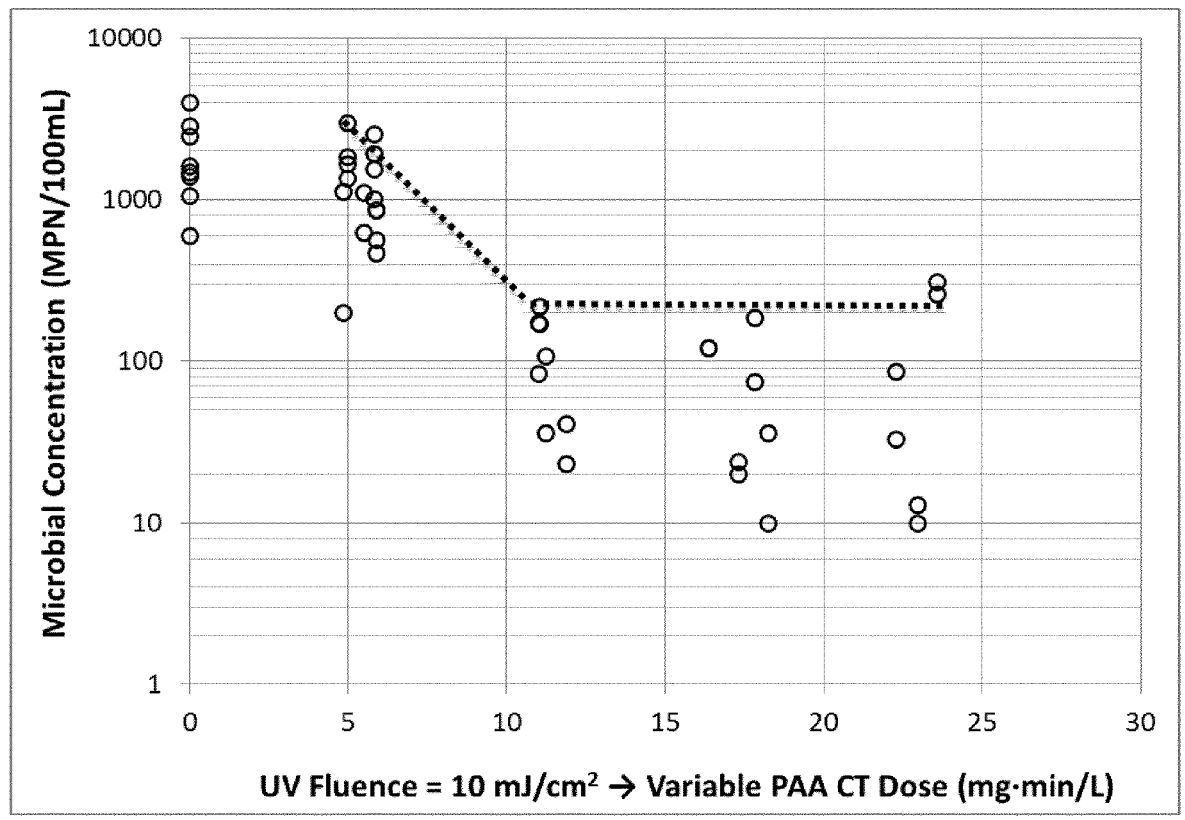
Figure 14: Inactivation of *E. coli* for UV→PAA treatment scenario where PAA treatment is preceded by a UV fluence of 10 mJ/cm$^2$. Dotted lines are illustrative to show general trend.

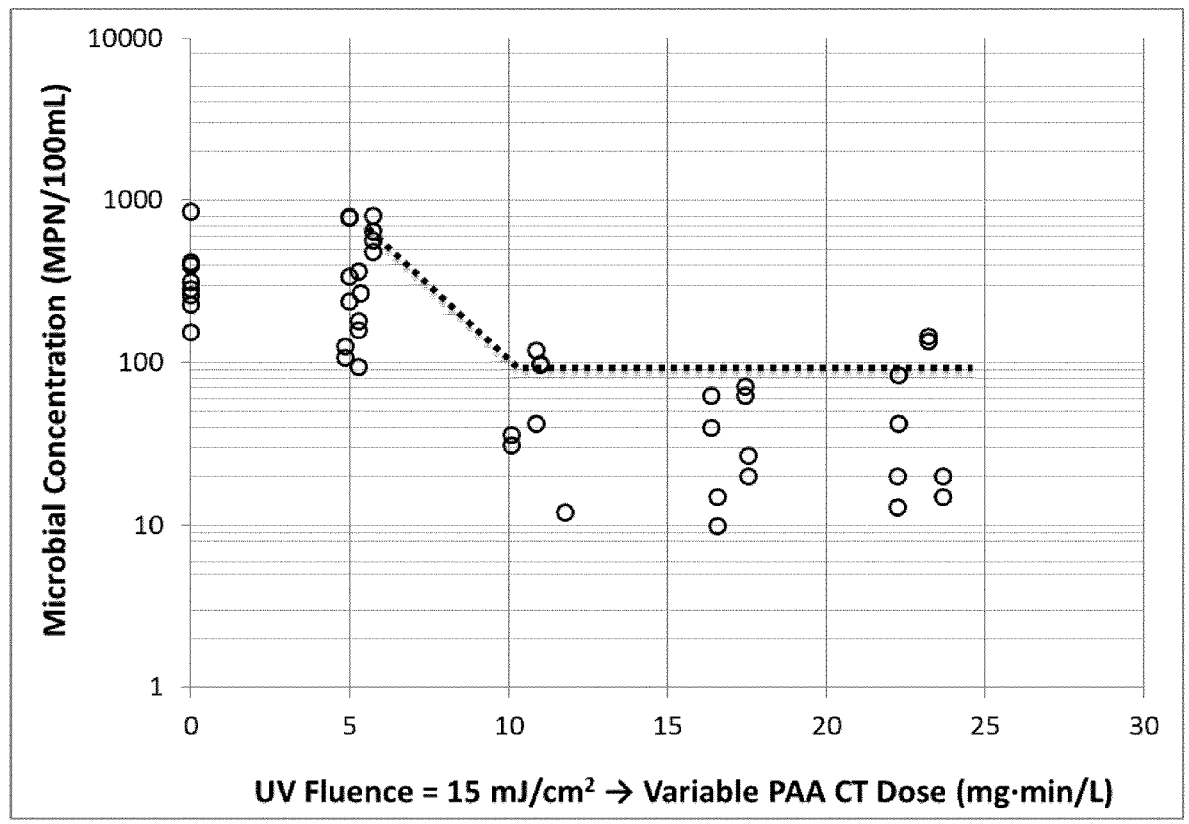
Figure 15: Inactivation of *E. coli* for UV→PAA treatment scenario where PAA treatment is preceded by a UV fluence of 15 mJ/cm$^2$. Dotted lines are illustrative to show general trend.

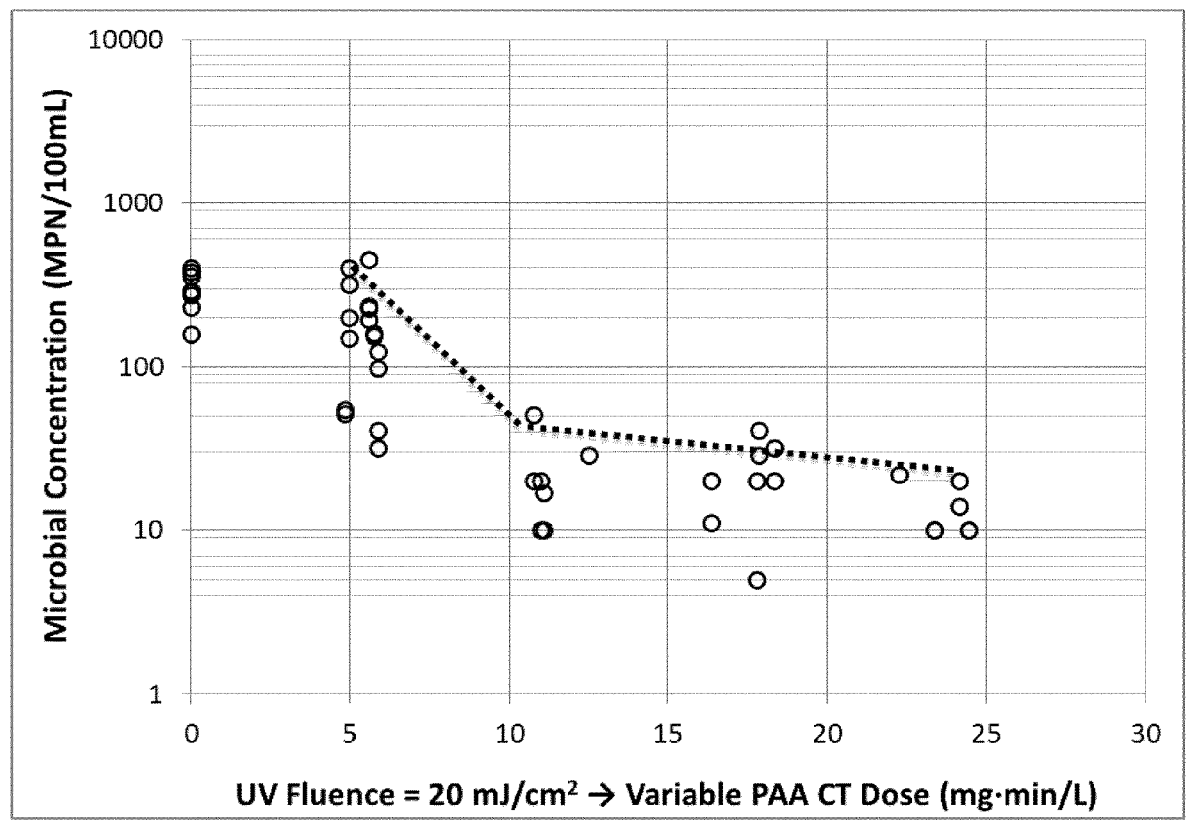
Figure 16: Inactivation of *E. coli* for UV→PAA treatment scenario where PAA treatment is preceded by a UV fluence of 20 mJ/cm². Dotted lines are illustrative to show general trend.

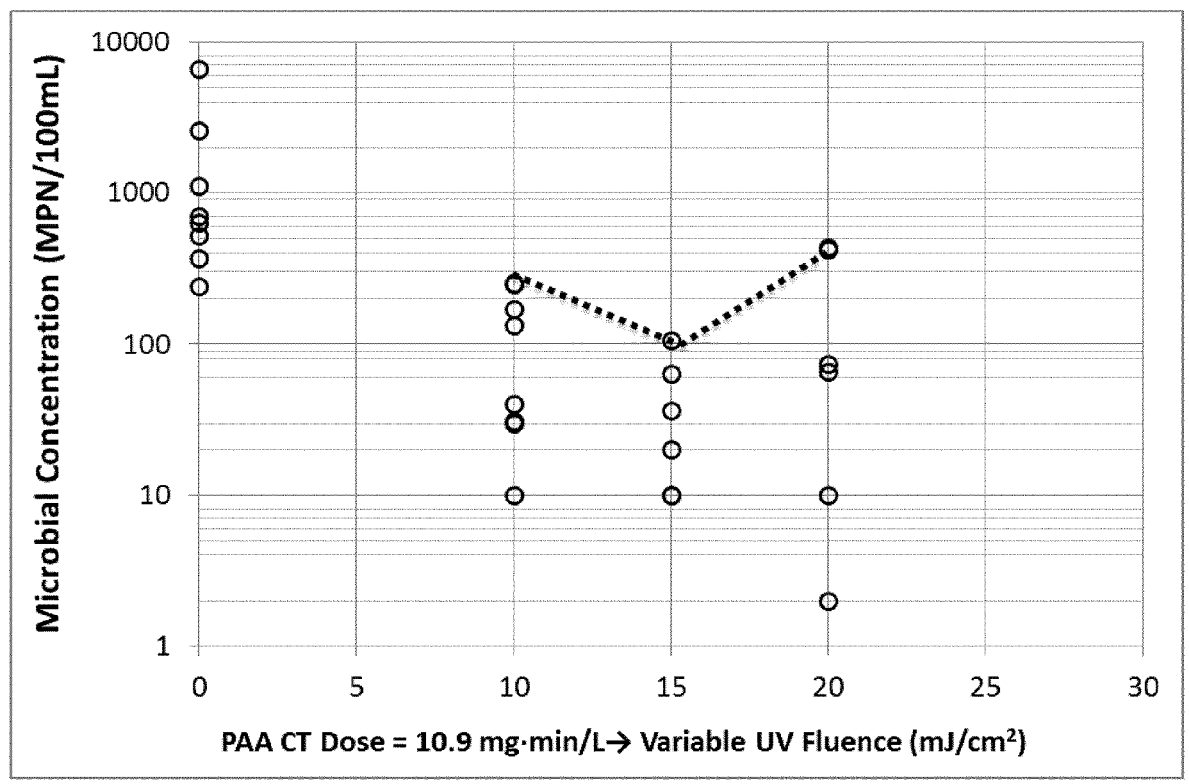
Figure 17: Inactivation of *E. coli* for PAA→UV treatment scenario where UV treatment is preceded by a PAA CT of 10.9 mg·min/L. Dotted lines are illustrative to show general trend.

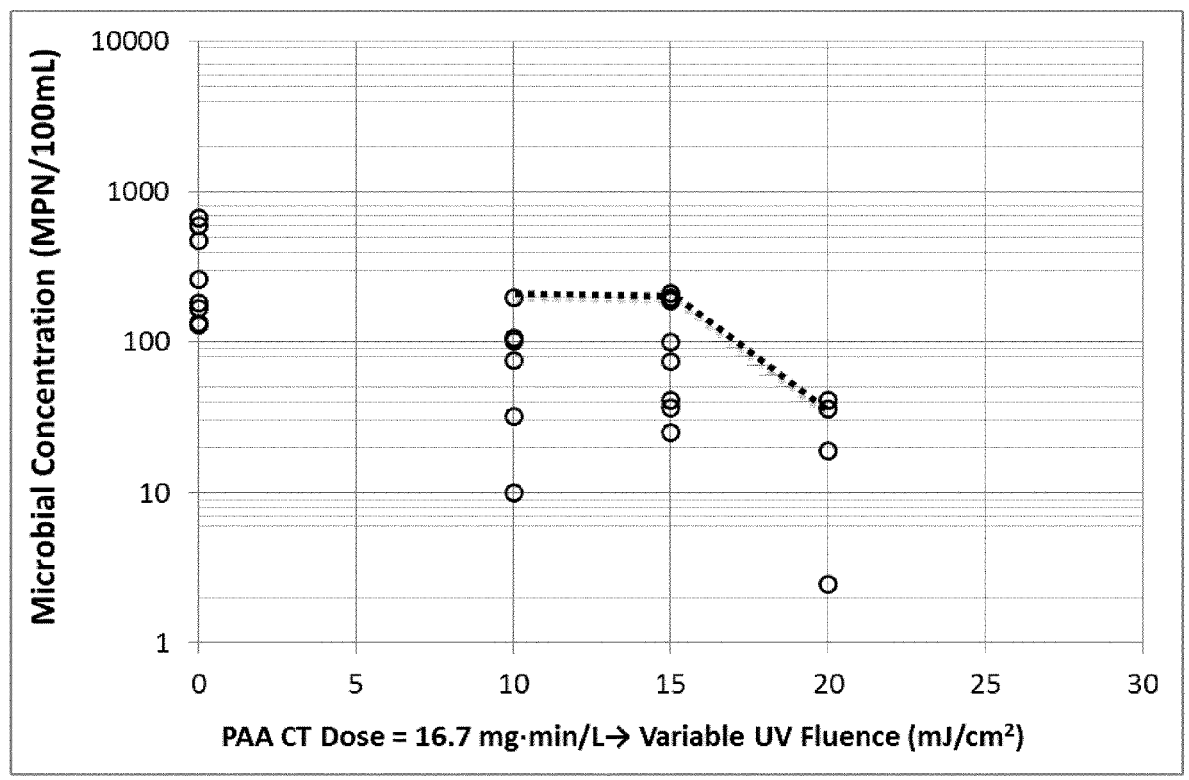
Figure 18: Inactivation of *E. coli* for PAA→UV treatment scenario where UV treatment is preceded by a PAA CT of 16.7 mg·min/L. Dotted lines are illustrative to show general trend.

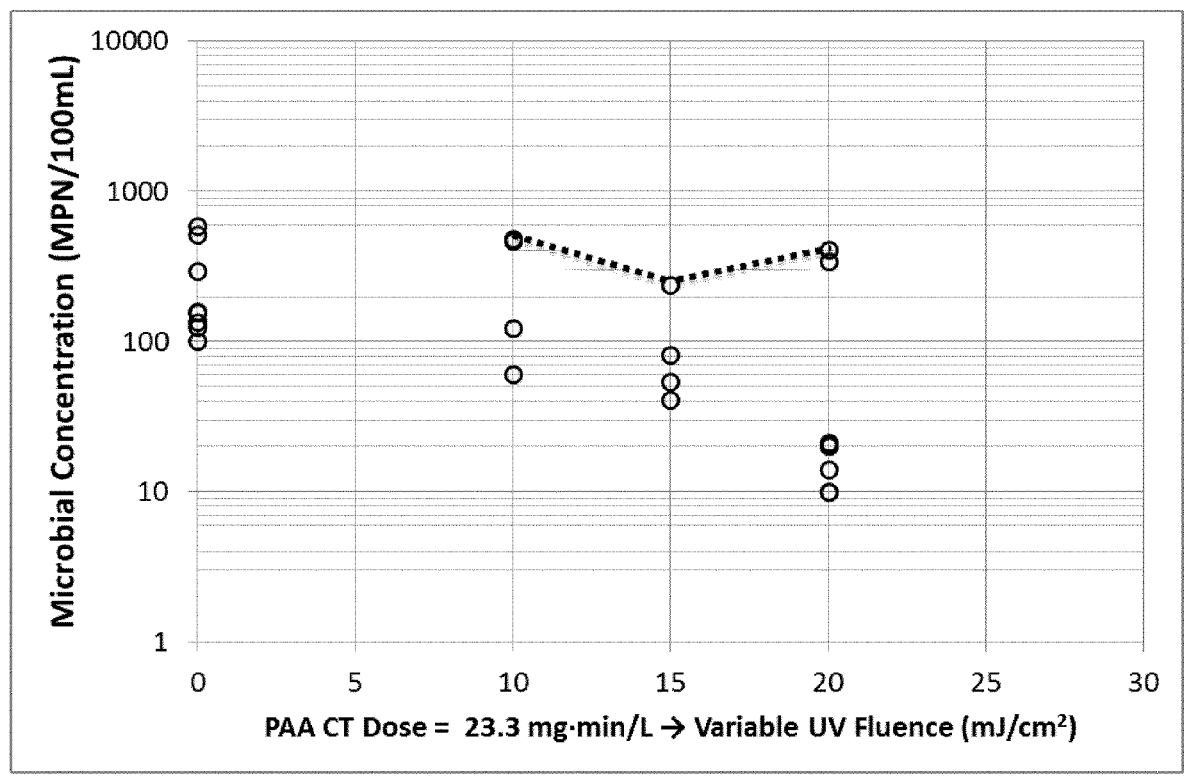
Figure 19: Inactivation of *E. coli* for PAA→UV treatment scenario where UV treatment is preceded by a PAA CT of 23.3 mg·min/L. Dotted lines are illustrative to show general trend.

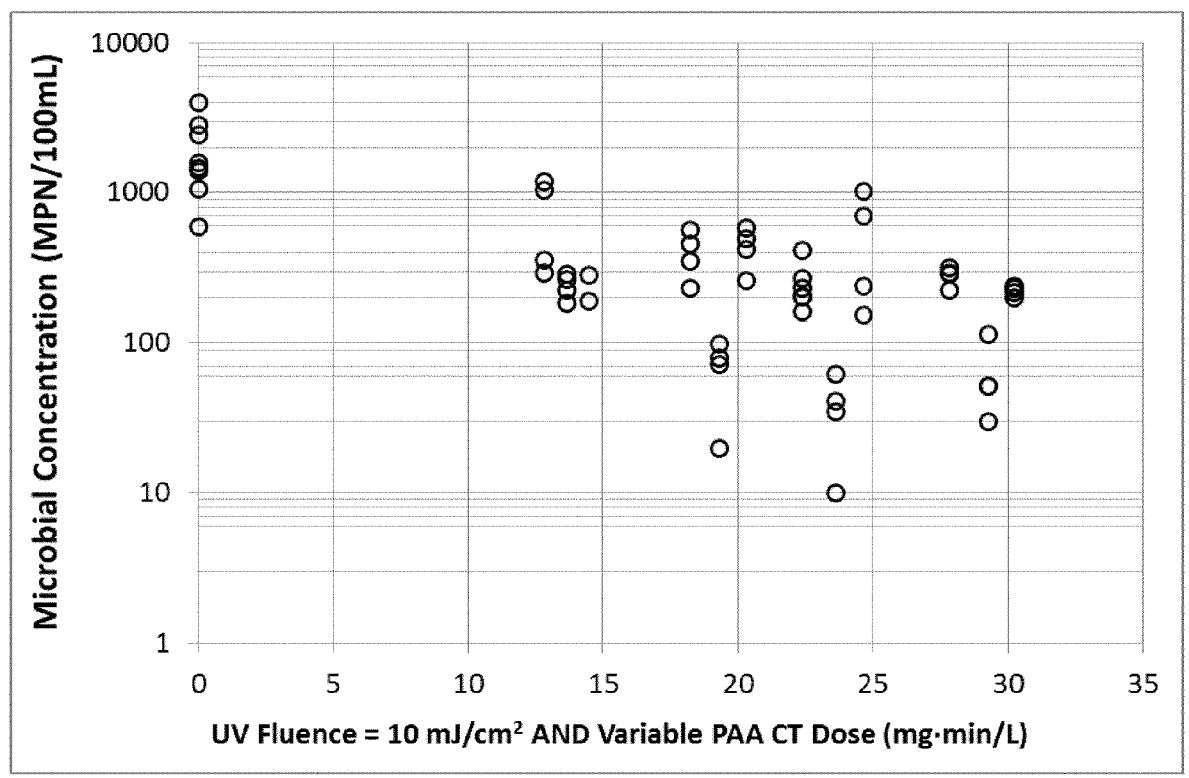
Figure 20: Inactivation of *E. coli* for UV+PAA treatment scenario where data is plotted for fixed UV fluences of 10 mJ/cm$^2$ and variable PAA CT doses.

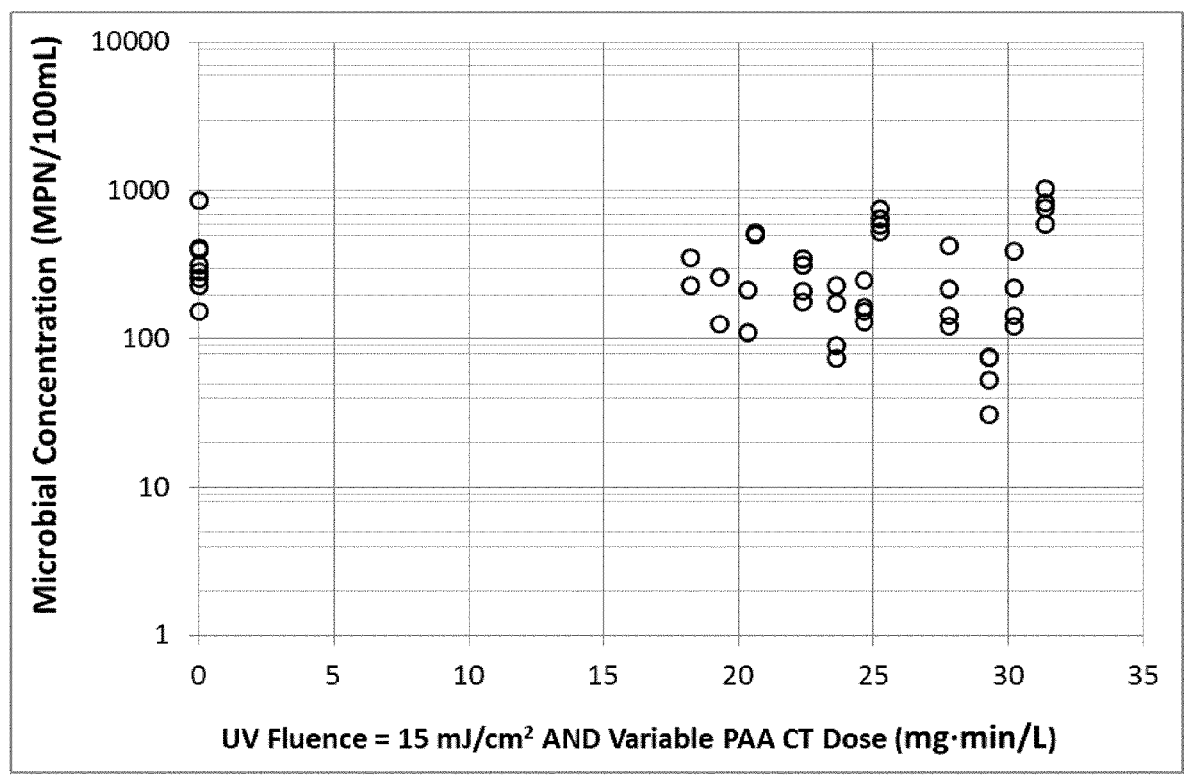
Figure 21: Inactivation of *E. coli* for UV+PAA treatment scenario where data is plotted for fixed UV fluences of 15 mJ/cm² and variable PAA CT doses.

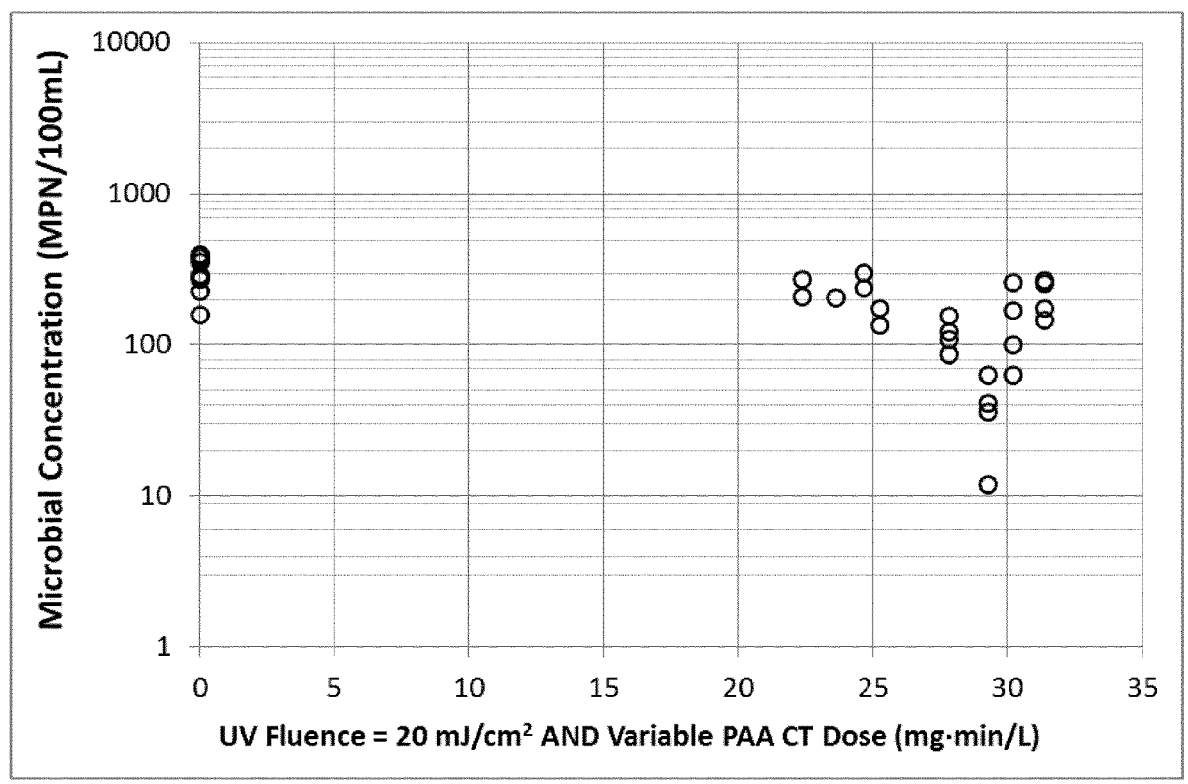
Figure 22: Inactivation of *E. coli* for UV+PAA treatment scenario where data is plotted for fixed UV fluences of 20 mJ/cm² and variable PAA CT doses.

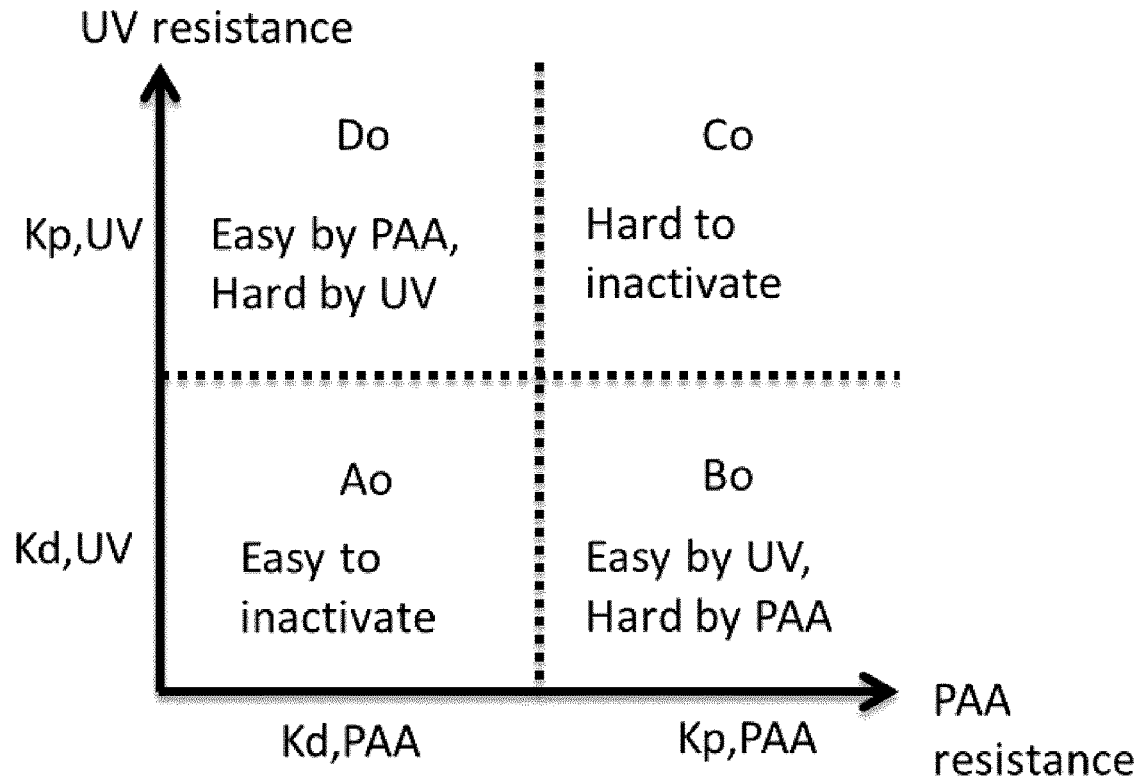
Figure 23: Four population mechanistic approach to model binary disinfection system consisting of UV and PAA disinfectants.
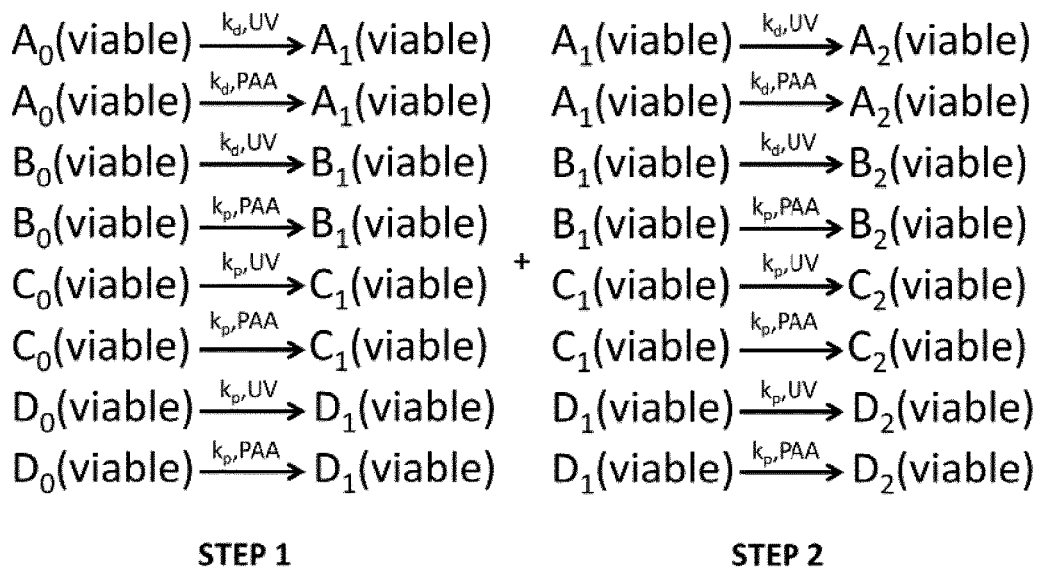
Figure 24: Inactivation mechanisms presenting the inactivation routes and respective first order inactivation rate constants for the proposed four population system with binary disinfectants.

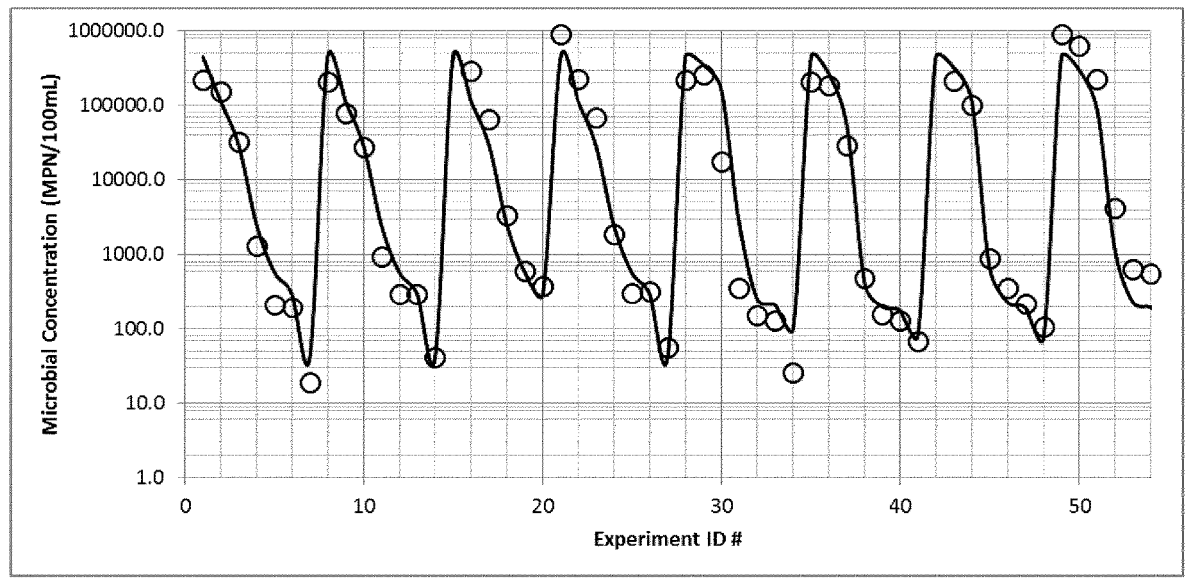
Figure 25: Experimental results from inactivation using UV or PAA alone (circles) and predicted values using the four population, binary disinfectant model.
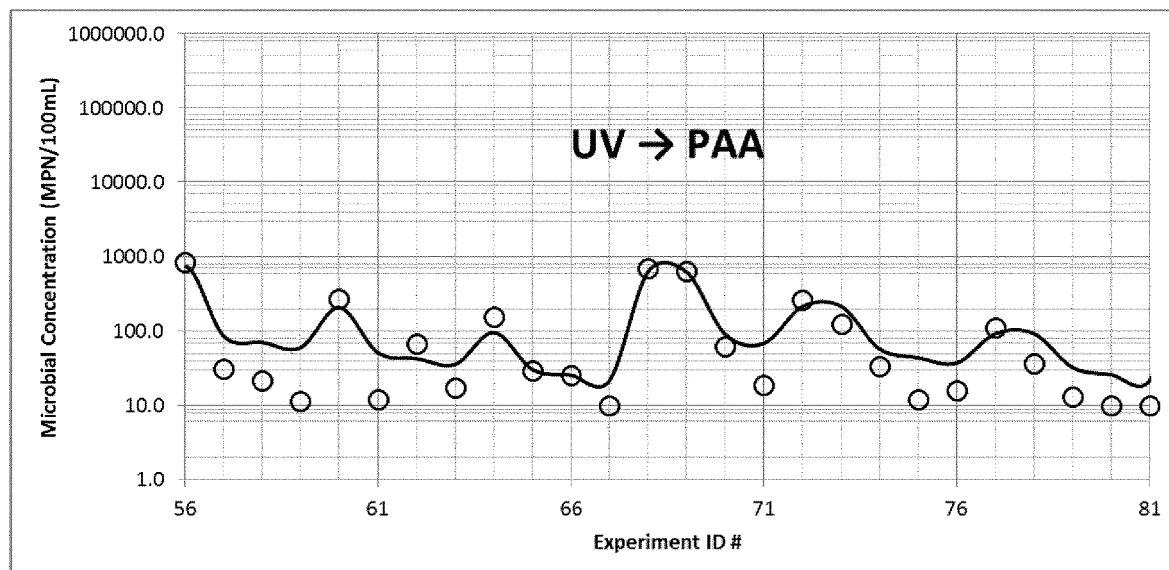
Figure 26: Experimental results from inactivation using UV→PAA (circles) and predicted values using the four population, binary disinfectant model.

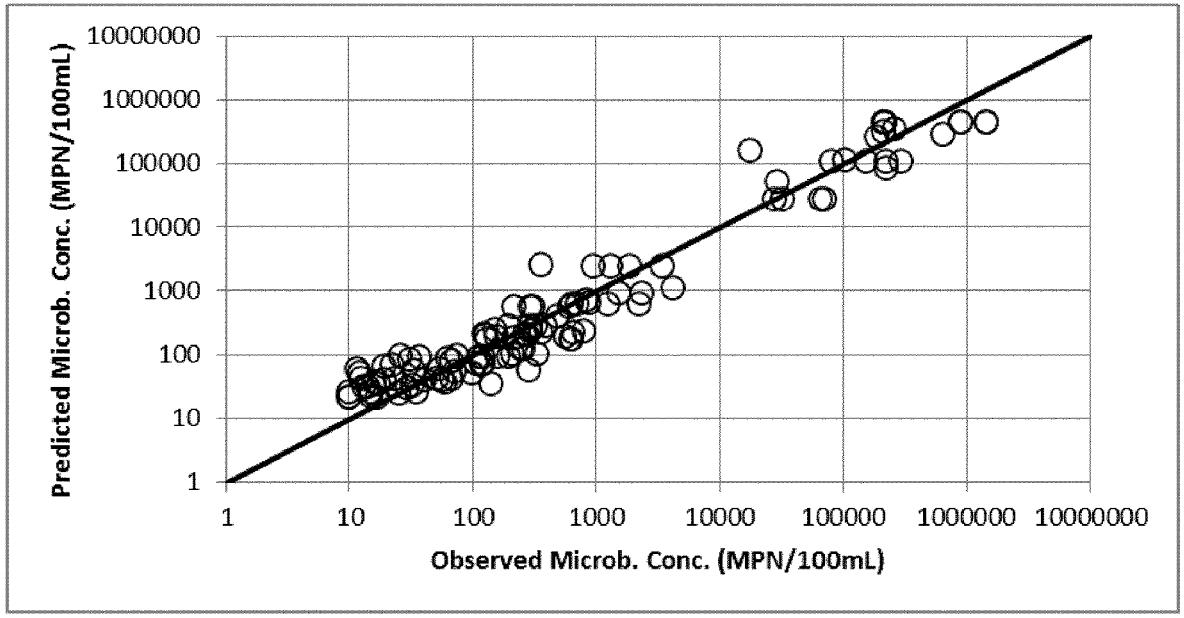
Figure 27: Observed versus model predicted combinations for the UV only, PAA only tests and sequential UV PAA tests. Diagonal line illustrates a perfect fit line.
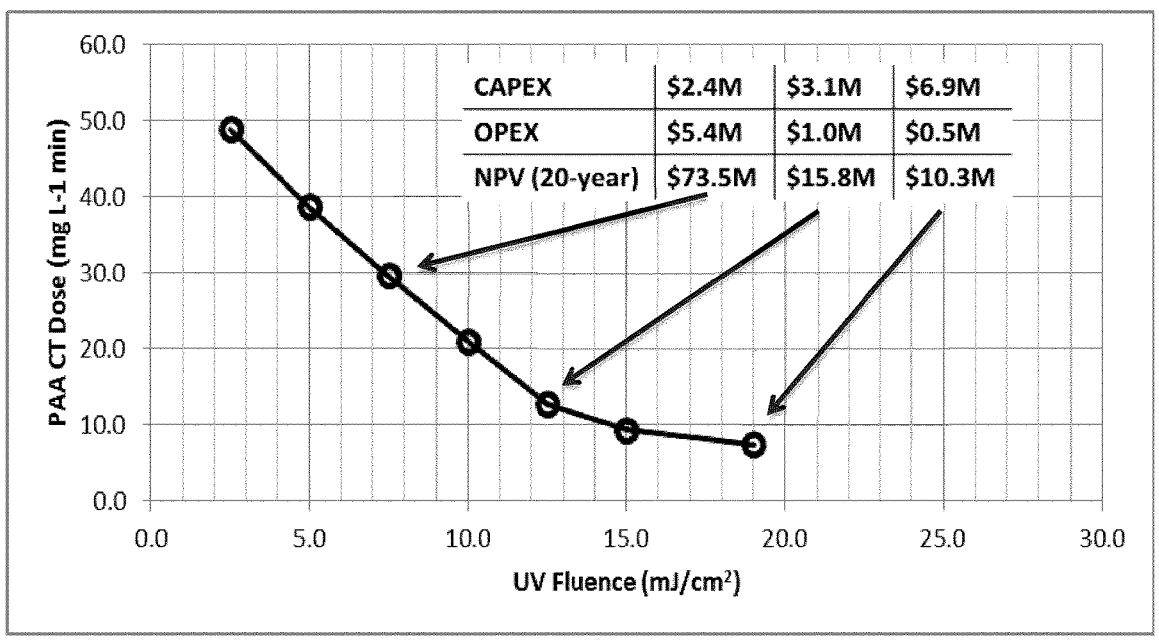
Figure 28: Model predicted combinations of PAA dose and UV fluence required to achieve an *E. coli* disinfection target of 63 cfu / 100 mL when applying the sequential UV→PAA treatment process.

FLUID DISINFECTION WITH ULTRAVIOLET RADIATION AND A CHEMICAL DISINFECTANT

CROSS-REFERENCE TO RELATED APPLICATION

The present application is a National Phase Entry of PCT International Application No. PCT/CA2016/050982, which was filed on Aug. 22, 2016, and claims the benefit under 35 U.S.C. § 119(e) of provisional patent application Ser. No. 62/207,734, filed Aug. 20, 2015, the contents of which are hereby incorporated by reference.

BACKGROUND OF THE INVENTION

Field of the Invention

In one of its aspects, the present invention relates to a system for treatment of a fluid (e.g., water). In another of its aspects, the present invention relates to a process for treatment of a fluid (e.g., water). More particularly, the present invention relates to a system for treatment of a fluid utilizing one or both ultraviolet (UV) radiation and a chemical disinfectant (e.g., peracetic acid (PAA)).

Description of the Prior Art

Chemical disinfection is an important component of water and wastewater treatment, and its effectiveness has been widely accepted since the introduction of chlorine disinfection for drinking water treatment in the late 1800's. When a suitable chemical is applied to water or wastewater with sufficient concentration and contact time (the product of these two factors defining the chemical disinfectant "dose"), chemical disinfection can effectively inactivate microorganisms and pathogens; thus protecting both consumers of water (i.e., public health) and the environment.

Similarly, the application of ultraviolet irradiation for disinfection of water and wastewater has increased dramatically over the last 30 years. This has been spurred by the potential for chemical disinfectant to form undesirable disinfection by-products. UV disinfection has employed throughout the drinking and wastewater treatment industry due to its efficacy for inactivating human pathogens, as well as providing a relatively low lifecycle cost in a small footprint. Inactivation of a pathogen or indicator microorganism occurs when photons of UV light are absorbed and cause damage to an organism's deoxyribonucleic acid (DNA) or ribonucleic acid (RNA), preventing reproduction.

Peroxyacids are a class of chemical disinfectants gaining attention due to the combined effects of: (i) high efficacy of inactivating organisms, (ii) formation of undesirable byproduct only in low concentrations, and (iii) rapid decay in the environment (i.e., after they have served their purpose as a disinfect). Peracetic acid (PAA) is a strong oxidant with a biocidal mode of action via cell membrane damage. Hydroxyl radicals (.OH) and reactive oxygen species released during decomposition reactions are believed to be secondary modes of action (Lubello et al., 2002). Peroxyacids, such as PAA, may also play a role in the disruption of the chemisomotic function of the lipoprotein cyctoplasmic membrane (Santoro et al., 2007, Baldry et al., 1989, Leaper, 1984).

Researchers have reported on the potential benefits of combining of UV and PAA to enhance the disinfection of municipal wastewater (Rajala-Mustonen et al. 1997, Caretti & Lubello 2003, Lubello et al. 2004, Heinonen-Tanksi 2005, Koivunen & Martin & Gehr 2007, Budde & Vineyard 2010, Gonzalez et al. 2012, Block & Tran 2015). However, the exact mechanism for this enhancement is not clear, and there is no general consensus on the mechanisms of disinfection that govern the application of a combined UV and PAA process.

It have been generally reported that the addition of PAA prior to UV irradiation increases inactivation through an advanced oxidation process (AOP), resulting from the photolysis of the O—O bond in the PAA molecule, generating a hydroxyl radical (.OH) (Caretti and Lubello 2003, Lubello et al. 2002). While investigating the combination of UV and PAA, Lubello et al. (2002) found a PAA concentration between 2 and 8 mg/L or a UV fluence of 120 to 300 mJ/cm$^2$ were unable to reach the target disinfection levels; however, when a PAA concentration of 2 mg/L was applied immediately before a UV fluence of 192 mJ/cm$^2$, over 4-log inactivation of total coliform was achieved. However, Gonzalez et al. (2012) reported that when peracetic acid and ultraviolet irradiation were combined, at a low UV fluence (13 mJ/cm$^2$), there was no synergistic benefit observed, when PAA was added either before or after UV irradiation.

The present inventors believe that these kind of results have presented challenges to practical implementation of a combination of UV and peracids such as PAA in commercial scale fluid (e.g., water) treatment systems. Thus, the present inventors believe there is still considerable ambiguity in the current understanding of the mechanisms of UV and PAA treatments preventing practical implementation of a combination of these treatments in commercial scale fluid (e.g., water) treatment systems.

In light of the above-mentioned deficiencies of the prior art, it would be highly desirable to have system and process for treatment of fluid (e.g., water) capable of being used for practical implementation of a combination of UV and peracids such as PAA in commercial scale fluid (e.g., water) treatment systems. It would also be desirable if the system could be used to design various aspects the fluid treatment system.

SUMMARY OF THE INVENTION

It is an object of the present invention to obviate or mitigate at least one of the above-mentioned disadvantages of the prior art.

It is another object of the present invention to provide a novel system for treatment of fluid (e.g., water) capable of being used for practical implementation of a combination of UV and peracids such as PAA in commercial scale fluid (e.g., water) treatment systems.

It is another object of the present invention to provide a novel process for treatment of fluid (e.g., water) capable of being used for practical implementation of a combination of UV and peracids such as PAA in commercial scale fluid (e.g., water) treatment systems.

Accordingly, in one of its aspects, the present invention provides an on-line device for controlling a fluid treatment process configured to inactivate a microorganism in a flow of fluid using ultraviolet radiation and a chemical disinfectant, the device comprising:

a memory for receiving a calculated database of dose response for the ultraviolet radiation and for the chemical disinfectant for a fluid treatment parameter;

means to obtain input data about the fluid treatment parameter from the process;

means to compare the input data with calculated database; and means to adjust one or more of the amount ultraviolet radiation and the chemical disinfectant added to the flow fluid in response to a difference between the input data and calculated database.

In another of its aspects, the present invention provides a process for controlling a fluid treatment process configured to inactivate a microorganism in a flow of fluid using ultraviolet radiation and a chemical disinfectant, the process comprising the steps of:

obtaining input data about a fluid treatment parameter;

comparing the input data with a calculated database of dose response for the ultraviolet radiation and for the chemical disinfectant for the fluid treatment parameter; and adjusting one or more of the amount ultraviolet radiation and the chemical disinfectant added to the flow fluid in response to a difference between the input data and calculated database.

The present device and process can be used to design to meet cost constraints—e.g., capital cost, operating costs, net present value (NPV), residual chemical concentrations, minimizing quenching requirements, optimizing fluid parameters for downstream treatment systems and the like. The fluid treatment parameter used in the present device and process can be any of these and/or can include ultraviolet transmittance (UVT) of the fluided being treated, fluid flow rate, fluid temperature, concentration of contaminants in the fluid and the like.

As described above, both ultraviolet (UV) irradiation and chemical disinfectant (e.g., a peracid such as peracetic acid (PAA) and performic acid (PFA), chlorine, chloramines and the like) are employed regularly for disinfecting water. Numerous constraints need to be considered when selecting, sizing and designing a single disinfectant and multiple disinfectant processes. The factors include one or more of the following:

the resistance to inactivation of the microrganisms to any single disinfectant;

the resistance to inactivation of the microrganisms to any combination of disinfectants;

the cost of any single disinfectant;

the cost of any combination of disinfectants;

the irradiation/contact time constraints of the site in consideration;

the space constraints of the site in consideration;

the impact of water quality parameters on any single disinfectant;

the impact of water quality parameters on any combination of disinfectants; and/or the effect of any one disinfectant on the effectiveness of a second disinfectant.

In the present invention, the combination of UV and chemical disinfectants (preferably peracid chemical disinfectants) is described including processes, methods and algorithms for selecting and sizing a multiple disinfection process. Non-limiting examples of chemical disinfectants that can be used in the present device and process include peracetic acid (PAA), chlorine, chloramine, chlorine dioxide, chlorite, ozone, performic acid, permanganate, persulfate, hydrogen peroxide, fenton reagents, ferric-based compounds, ferrous-based compounds, alum-based compounds, polymer coagulants, polymer flocculants, free nitrous acid and any mixture of two or more of these. The algorithms and methods are applied to in order to meet any one of the following criteria (also, any combination of these criteria can be used to define a new sizing criterion):

minimizing the capital cost of the multiple disinfection process;

minimizing the operating cost of the multiple disinfection process;

minimizing the footprint of the multiple disinfection process;

minimizing the time required for the multiple disinfection process;

minimizing the side-effects (i.e., disinfection byproducts formation, etc.) of multiple disinfection processes minimizing the impact of water quality on regulated effluent limits; and/or minimizing the setpoints of multiple disinfectants.

BRIEF DESCRIPTION OF THE DRAWINGS

Embodiments of the present invention will be described with reference to the accompanying drawings, wherein like reference numerals denote like parts, and in which:

FIG. 1 illustrates a first embodiment of the present process useful for sizing and selection of combined UV and peracid water disinfection process;

FIG. 2 illustrates a second embodiment of the present process useful for sizing and selection of combined UV and peracid water disinfection process;

FIG. 3 illustrates a third embodiment of the present process useful for sizing and selection of combined UV and peracid water disinfection process;

FIG. 4 illustrates a first embodiment of the present process useful for sizing and selection of combined UV and peracid water disinfection process;

FIG. 5 illustrates a schematic in the form of a bucket of water microorganims consisting of four different populations of microganisms with varying resistance to UV or PAA;

FIG. 6 illustrates schematic shown in FIG. 5 with reference to a sample cost associated with removing 20 colonies by UV alone;

FIG. 7 illustrates schematic shown in FIG. 5 with reference to a sample cost associated with removing 20 colonies by PAA alone;

FIG. 8 illustrates schematic shown in FIG. 5 with reference to a sample cost associated with removing 20 colonies by 50% PAA and 50% UV;

FIG. 9 illustrates schematic shown in FIG. 5 with reference to a sample cost associated with removing 20 colonies using a preferred embodiment of the present process and system;

FIG. 10 illustrates PAA demand/decay for 22% and 15% PAA solutions added to water samples from the plant trial reported below at CO=5 mg/L (top) wherein the data was modeled (black lines) from experimental results using Equation 1, and microbial inactivation of water samples from the plant trial reported below treated with 22% and 15% PAA solutions at a CO=5 mg/L (bottom);

FIG. 11 illustrates PAA demand/decay model plots for water samples collected on two days during the plant trial reported below (model curves generated from experimental results using Equation 1);

FIG. 12 illustrates inactivation of $E.\ coli$ using PAA for water samples collected on two days during the plant trial reported below (top) and an inactivation curve for poorest inactivation levels measured for water samples on two days during the plant trial reported below (bottom);

FIG. 13 illustrates Inactivation of $E.\ coli$ using UV for water samples collected in two separate years at the water treatment plant referred to below with respect to the plant trial—inactivation curves for all data points (top) and poorest inactivation levels (bottom);

FIGS. 14-19 each illustrate inactivation of *E. coli* for a UV→PAA treatment scenario where PAA treatment is preceded by a particular UV fluence and/or PAA CT (dotted lines are illustrative to show general trend);

FIGS. 20-22 each illustrate inactivation of *E. coli* for a UV+PAA treatment scenario where data is plotted for various fixed UV fluences and variable PAA CT doses;

FIG. 23 illustrates a four population mechanistic approach to model a dual disinfection system consisting of UV and PAA disinfectants;

FIG. 24 illustrates inactivation mechanisms presenting the inactivation routes and respective first order inactivation rate constants for the four population system with dual disinfectants illustrated in FIG. 23;

FIG. 25 illustrates the experimental results from inactivation using UV or PAA alone (circles) and predicted values using the four population, dual disinfectant model illustrated in FIG. 23;

FIG. 26 illustrates the experimental results from inactivation using UV→PAA (circles) and predicted values using the four population, dual disinfectant model illustrated in FIG. 23;

FIG. 27 illustrates observed versus model predicted combinations for the UV only, PAA only tests and sequential UV PAA tests (the diagonal line illustrates a perfect fit line); and FIG. 28 illustrates model predicted combinations of PAA dose and UV fluence required to achieve an *E. coli* disinfection target of 63 cfu/100 mL when applying the sequential UV→PAA treatment process.

DETAILED DESCRIPTION OF THE PREFERRED EMBODIMENTS

In one of its aspects, the present invention relates to an on-line device for controlling a fluid treatment process configured to inactivate a microorganism in a flow of fluid using ultraviolet radiation and a chemical disinfectant, the device comprising: a memory for receiving a calculated database of dose response for the ultraviolet radiation and for the chemical disinfectant for a fluid treatment parameter; means to obtain input data about the fluid treatment parameter from the process; means to compare the input data with calculated database; and means to adjust one or more of the amount ultraviolet radiation and the chemical disinfectant added to the flow fluid in response to a difference between the input data and calculated database. Preferred embodiments of this device may include any one or a combination of any two or more of any of the following features:
  the chemical disinfectant is a peracid;
  the chemical disinfectant is peracetic acid (PAA);
  the fluid treatment parameter is the operating cost to treat the flow of flow.
  the fluid treatment parameter is the cost of ultraviolet radiation to treat the flow of fluid;
  the fluid treatment parameter is the cost of the chemical disinfectant to treat the flow of fluid;
  the fluid treatment parameter is the cost of the the ultraviolet radition and the chemical disinfectant to treat the flow of fluid;
  the fluid treatment parameter is the cost of electricity to treat the flow of fluid;
  the fluid treatment parameter is the daily volume fluid treated by the fluid treatment parameter;
  the calculated database is based on empirical data obtained from a chemical disinfectant dose response curve for the fluid treatment parameter;
  the calculated database is based on empirical data obtained from a chemical disinfectant dose response curve for the fluid treatment parameter;
  the calculated database is based on empirical data obtained from a chemical disinfectant dose response curve for the fluid treatment parameter and data obtained from a chemical disinfectant dose response curve for the fluid treatment parameter;
  the fluid treatment process is configured to inactivate the microorganism in the flow of fluid using ultraviolet radiation and the chemical disinfectant concurrently;
  the fluid treatment process is configured to inactivate the microorganism in the flow of fluid using ultraviolet radiation and the chemical disinfectant sequentially;
  the fluid treatment process is configured to inactivate the microorganism in the flow of fluid using ultraviolet radiation prior to the chemical disinfectant; and/or
  the fluid treatment process is configured to inactivate the microorganism in the flow of fluid using ultraviolet radiation after the chemical disinfectant.

In another of its aspects, the present invention relates to a process for controlling a fluid treatment process configured to inactivate a microorganism in a flow of fluid using ultraviolet radiation and a chemical disinfectant, the process comprising the steps of: obtaining input data about a fluid treatment parameter; comparing the input data with a calculated database of dose response for the ultraviolet radiation and for the chemical disinfectant for the fluid treatment parameter; and adjusting one or more of the amount ultraviolet radiation and the chemical disinfectant added to the flow fluid in response to a difference between the input data and calculated database. Preferred embodiments of this device may include any one or a combination of any two or more of any of the following features:
  the chemical disinfectant is a peracid;
  the chemical disinfectant is peracetic acid (PAA);
  the fluid treatment parameter is the operating cost to treat the flow of flow;
  the fluid treatment parameter is the cost of ultraviolet radiation to treat the flow of fluid;
  the fluid treatment parameter is the cost of the chemical disinfectant to treat the flow of fluid;
  the fluid treatment parameter is the cost of the the ultraviolet radition and the chemical disinfectant to treat the flow of fluid;
  the fluid treatment parameter is the cost of electricity to treat the flow of fluid;
  the fluid treatment parameter is the daily volume fluid treated by the fluid treatment parameter;
  the calculated database is based on empirical data obtained from a chemical disinfectant dose response curve for the fluid treatment parameter;
  the calculated database is based on empirical data obtained from a chemical disinfectant dose response curve for the fluid treatment parameter;
  the calculated database is based on empirical data obtained from a chemical disinfectant dose response curve for the fluid treatment parameter and data obtained from a chemical disinfectant dose response curve for the fluid treatment parameter;
  the fluid treatment process is configured to inactivate the microorganism in the flow of fluid using ultraviolet radiation and the chemical disinfectant concurrently;

the fluid treatment process is configured to inactivate the microorganism in the flow of fluid using ultraviolet radiation and the chemical disinfectant sequentially;

the fluid treatment process is configured to inactivate the microorganism in the flow of fluid using ultraviolet radiation prior to the chemical disinfectant; and/or the fluid treatment process is configured to inactivate the microorganism in the flow of fluid using ultraviolet radiation after the chemical disinfectant.

The selection of order and sizing of the UV and chemical disinfection processes can depend on the disinfection kinetics of each disinfectant alone as well as potential synergies. In the present system and process a calculated database of dose response for the ultraviolet radiation and for the chemical disinfectant for a fluid treatment parameter is created.

Preferably, this database using the following steps:
(1) First, the dose response curve of each individual disinfectant is measured or assumed.
(2) The log inactivation of microorganisms is plotted on the y-axis against an x-axis that including a treatment constraint. A treatment constraint could be, for example, the cost of treatment, time required for treatment, energy demand of the treatment and/or the footprint of the fluid treatment system.
(3) An algorithm is used to determine the sequence and amount of disinfectant dose where the disinfectant with the fastest kinetics (i.e., greatest slope) is always selected in order to minimize the treatment constraint.
(4) Dose response curves are also generated for the combinations of UV and peracid disinfectants; with each disinfectant applied sequentially in both orders and simultaneously. The dose response curves are compared and the addition sequence for the best curve for that system, disinfectant, etc. is selected.
(5) The disinfectant is applied to the fluid (e.g., water) to be treated at the calculated dose.

By determining the kinetics of each disinfectant alone, using the concept of multi-target disinfection exemplified below, it is possible to emperically determine the optimal sequence of the two disinfectants and the relative amount that minimizes overall treatment constraint (e.g. cost, footprint, energy demand, or time)—i.e., to create the above-mentioned calculated database of dose response for the ultraviolet radiation and for the chemical disinfectant for a fluid treatment parameter is created. The algorithm is able to also take into account other synergistic behaviors occurring between the two disinfectants as long as they are shown in the dose response curves of the two disinfectants (alone and/or in combination).

FIG. 4 illustrates a first embodiment of the above approach. In this scenario, given the slope of the fast and slow regimes of the UV and PAA kinetics, the best combination is PAA first (to give the amount of kill noted on the left as PAA dose) and UV after (to give the amount of kill noted on the left as UV dose).

In this first embodiment, the amount of PAA applied before UV may be up to about 10 mg/L, up to about 100 mg/L or up to about 1000 mg/L. The CT dose of PAA applied before UV may be up about 10 mg/L min, up to about 100 mg/L min or up to about 1000 mg/L min. The contact time of PAA applied before UV may be up to about 1 min, up to about 10 min, up to about 100 min or up to about 1000 min. The dose of UV applied after PAA may be up to about 5 $mJ/cm^2$, up to about 10 $mJ/cm^2$, up to about 20 $mJ/cm^2$, up to about 40 $mJ/cm^2$, up to about 100 $mJ/cm^2$ or up to about 1000 $mJ/cm^2$.

FIG. 2 illustrates a second embodiment of the above approach. In this scenario, given the slope of the fast and slow regimes of the UV and PAA kinetics, the best combination is UV first (to give the amount of kill noted on the left as UV dose) and PAA after (to give the amount of kill noted on the left as PAA dose).

In this second embodiment, the amount of PAA applied after UV may be up to about 10 mg/L, up to about 100 mg/L or up to about 1000 mg/L. The CT dose of PAA applied after UV may be up about 10 mg/L min, up to about 100 mg/L min or up to about 1000 mg/L min. The contact time of PAA applied after UV may be up to about 1 min, up to about 10 min, up to about 100 min or up to about 1000 min. The dose of UV applied before PAA may be up to about 5 $mJ/cm^2$, up to about 10 $mJ/cm^2$, up to about 20 $mJ/cm^2$, up to about 40 $mJ/cm^2$, up to about 100 $mJ/cm^2$ or up to about 1000 $mJ/cm^2$.

FIG. 3 illustrates a third embodiment of the above approach. In this scenario, given the slope of the fast and slow regimes of the UV and PAA kinetics, the best combination is PAA first (to give the amount of kill noted on the left as PAA dose 1) followed by UV after (to give the amount of kill noted on the left as UV dose), followed by PAA dose after (to give the amount of kill noted on the left as PAA dose 2).

In this third embodiment, the amount of PAA applied first before UV may be up to about 10 mg/L, up to about 100 mg/L or up to about 1000 mg/L. The CT dose of PAA applied first before UV may be up about 10 mg/L min, up to about 100 mg/L min or up to about 1000 mg/L min. The contact time of PAA applied first before UV may be up to about 1 min, up to about 10 min, up to about 100 min or up to about 1000 min. The dose of UV applied between PAA dosages may be up to about 5 $mJ/cm^2$, up to about 10 $mJ/cm^2$, up to about 20 $mJ/cm^2$, up to about 40 $mJ/cm^2$, up to about 100 $mJ/cm^2$ or up to about 1000 $mJ/cm^2$.

FIG. 4 illustrates a fourth embodiment of the above approach. In this scenario, different populations of microorganisms display different resistance to UV and PAA disinfection. Neither disinfectant alone can reach the treatment goal in a feasible manner. Here the best combination is to apply UV disinfection until tailing occurs, thereby only leaving behind UV resistant microorganisms. Then PAA is applied to inactivate the remaining microorganisms that are susceptible to PAA.

In this fourth embodiment, the amount of PAA applied after UV may be up to about 10 mg/L, up to about 100 mg/L or up to about 1000 mg/L. The CT dose of PAA applied after UV may be up about 10 mg/L min, up to about 100 mg/L min or up to about 1000 mg/L min. The contact time of PAA applied after UV may be up to about 1 min, up to about 10 min, up to about 100 min or up to about 1000 min. The dose of UV applied before PAA may be up to about 5 $mJ/cm^2$, up to about 10 $mJ/cm^2$, up to about 20 $mJ/cm^2$, up to about 40 $mJ/cm^2$, up to about 100 $mJ/cm^2$ or up to about 1000 $mJ/cm^2$.

To father illustrate this concept, reference is made to a "bucket" of water consisting of four different populations of microorganisms each of a varying number (FIG. 5). Each population of microorganism has a specific resistance to UV or PAA, defined as the dollar value required to disinfect that population of microorganisms.

If no method or algorithm were applied and/or single disinfectants were applied the following would be the resulting treatment costs for the scenarios illustrated in FIGS. 6-8.

In contrast, applying the preferred embodiment of the present system and method results in the lowest cost of treatment as shows in FIG. 9.

Embodiments of the present invention will be illustrated with reference to the following example of a trial at a municipal wastewater treatment plant (WWTP) which should not be used to construe or limit the scope of the present invention.

The examined WWTP is located in the southeastern region of the United States. At the time of this investigation, the facility was treating an average flow of 70 million gallons per day (MGD) due to the closing of a nearby wet corn milling facility. The current liquid treatment process consists of coarse bar screens, grit removal, recently installed fine bar screens, primary clarification, high-rate biotowers, activated sludge and secondary clarification. Biosolids treatment consists of anaerobic digestion and dewatering with the final disposition of solids being land application and a surface disposal site.

The facility was interested in pursuing potential changes needed to meet discharge permit requirements at the design flow of 90 MGD.

Materials and Methods

To investigate the feasibility and economics of implementing a combined disinfection technology strategy (UV+PAA), bench testing was conducted to inform process selection and sizing. Samples of secondary effluent were collected twice daily (7:00 and 13:00) immediately prior to the discharge from the plant and were treated at bench-scale, on site. Different operational scenarios were evaluated including the following five combinations: PAA alone, UV alone, PAA followed by UV, UV followed by PAA, and simultaneous UV and PAA.

In this study, the sequential and simultaneous use of UV and PAA disinfectants was investigated. The present inventors believed that the effluent at the WWTP would be a good candidate for this combination treatment because of its low UVT, high initial *Escherichia coli* (*E. coli*) concentrations ($10^5$-$10^6$ most probable number (MPN)/100 mL), and high and variable PAA demand and decay.

Analytical Methods

Table 1 provides a summary of the parameters measures and analytical methods employed for the bench-scale treatability study.

TABLE 1

Summary of analytical methods used.

| Parameter | Analytical Method | Instrument |
|---|---|---|
| TSS | Standard Method 2504 | n/a |
| COD | Standard Method 5220 | n/a |
| UVT | Standard Method 5910 | Hach DR500 at 254 nm |
| Color | Standard Method 2120 | Hach DR500 at 455 nm |
| BOD5 | Standard Method 5210 | n/a |
| PAA concentration | DPD method | CHEMetrics vacu-vials and Single-Analyte-Photometer |
| E. coli concentration | Standard Method 9223 | IDEXX Colisure |

Bench Test Protocols

In this study, secondary effluent samples were collected and treated with PAA to achieve residual concentration*contact time (CTs) of 2.5-50 mg·min/L. PAA tests were conducted in clean glass beakers (500 or 2000 mL), and mixed continuously using a magnetic stirrer (600 rpm). Measurements of PAA residuals were collected over time, and *E. coli* samples were collected following PAA quenching using sodium bisulfite. The four samples collected between September 22-24 were each treated with PAA ($C_O$=5.0 mg/L) in order to estimate the demand/decay for each sample. These results were then used to estimate the contact times needed to achieve CT doses ranging from 2.5-50 mg·min/L for each sample. The demand/decay kinetic parameters were recalculated using the experimental results from each inactivation experiment.

UV testing was conducted using a conventional collimated beam (CB) apparatus. UV irradiation was measured using an International Light Technologies (ILT) ILT1700 radiometer with a UV detector calibrated at 253.7 nm (monochromatic output of low-pressure mercury amalgam lamp). Samples were irradiated in order to achieve UV fluences of 2.5, 5, 10, 15, 20 and 40 mJ/cm$^2$. Calculations of the fluence were based on standardized method for fluence determination presented by Bolton & Linden (2003).

For the UV+PAA experiment, effluent was first irradiated to UV fluences of 10, 15 or 20 mJ/cm$^2$, then dosed with PAA as described above. For the PAA+UV experiment, effluent was first dosed with PAA as described above. After set durations, portions of the sample were removed, PAA quenched with sodium bisulfite, and then subjected to UV fluences of 10, 15 or 20 mJ/cm$^2$. For the simultaneous PAA+UV experiment, two different scenarios were investigated. The first involved dosing PAA at the onset of UV irradiation, irradiating for a set duration, and then removing the sample from UV exposure and continuing to stir until a desired PAA contact time was achieved. The second scenario involved first dosing PAA and allowing it to stir for a period prior to subjecting it to UV irradiation.

The full test plan and experimental matrix is included in Appendix A.

Data Analyses

PAA Decomposition Kinetics

PAA residuals were fitted to a demand/decay curve using Equation 1. The PAA CT (mg·min/L) was determined by integrating the area under the demand/decay curve and is calculated using Equation 2.

$$C = (C_0 - D)e^{-kt} \quad \text{[Equation 1]}$$

where,
C is the concentration of PAA (mg/L) at time t (min)
$C_0$ is initial concentration of PAA (mg/L)
D is the instantaneous demand of PAA (mg/L)
k is the decay rate constant of PAA (1/min)
t is the contact time (min)

$$CT = \frac{C_D - D}{k}(1 - e^{-kt}) \quad \text{[Equation 2]}$$

where,
CT is the integral PAA dose (concentration*contact time); mg·min/L (Santoro et al., 2015)

PAA and UV Disinfection Kinetics

The models that are used for disinfection for PAA and UV disinfection when used individually are well known such as the Chick-Watson model and the Hom's model. PAA disinfection can be evaluated as a function of residual and contact time. The disinfection kinetics of microorganisms is conventionally modelled by relating the extent of inactivation of the microorganisms to the products of the disinfectant dose and the contact time. For the PAA process the product of dose and contact time is the defined as the CT (mg·min/L) while for UV the product of dose and contact time is the UV fluence (mW*sec/cm$^2$). That said, the present inventors are not aware of a published model for evaluating a combined PAA and UV disinfection process and the development of such a model is believed to be shown for the first time in this specification.

To develop an disinfection kinetic model, the concentration of viable for *E. coli* can be plotted against either PAA—CT dose or UV fluence and the data fitted using the double exponential inactivation model, described in Equation 3.

$$N = N_d e^{-k_d DOSE^m} + N_p e^{-k_p DOSE} \quad \text{[Equation 3]}$$

where,

N is the total concentration of viable *E. coli*; MPN/100 mL $N_d$ is the concentration of particle-associated *E. coli*; MPN/100 mL $N_p$ is the concentration of dispersed *E. coli*; MPN/100 mL $k_d$ is the first order inactivation rate constant for particle-associated *E. coli*; for PAA=L/mg·min, for UV=cm²/mJ $k_p$ is the first order inactivation rate constant for dispersed *E. coli*; for PAA=L/mg·min, for UV=cm²/mJ m is an inactivation kinetic model parameter describing shoulder effects (m=1 for with UV doses)

DOSE is the dose; for PAA=mg·min/L, for UV=mJ/cm²

Results and Discussion

The results and discussion are presented in below in five sections: (1) water quality testing, (2) PAA disinfection testing, (3) UV disinfection testing, (4) combined UV and PAA disinfection testing, and (5) modelling the disinfection kinetics of the sequential UV→PAA process. Each section presented results from the experiments conducted as well as sizing calculations for the UV and PAA disinfection processes to meet the plant's disinfection targets.

General Water Quality

Each of the four samples collected over the 2 day period was analyzed for UVT, color, TSS, COD and BOD. The results of these tests are summarized in Table 2. The water quality was fairly consistent among the samples and was not affected by the flow rate in the plant.

TABLE 2

WWTP secondary effluent water quality.

| Sample ID | Plant Flow (mgd) | UVT (%) | Color (PtCo) | TSS (mg/L) | COD (mg/L) | BOD (mg/L) |
|---|---|---|---|---|---|---|
| Sept. 22 - AM | 60.6 | 19.5 | 175 | 16 | 115 | 20 |
| Sept. 22 - PM | 56.7 | 20.8 | 160 | 14 | 111 | 16 |
| Sept. 24 - AM | 62.5 | 20.2 | 188 | 16 | 114 | 20 |
| Sept. 24 - PM | 109.5 | 20.1 | 169 | 17 | 109 | 16 |

PAA Disinfection Tests

There are several different commercial formulations of PAA available, with differing concentrations of PAA and hydrogen peroxide. For this study, a 22 wt % solution of PAA was used for testing. To provide that this formulation of PAA would be suitable for use, it was compared with a 15 wt % PAA formula. The demand/decay kinetics, as well as microbial inactivation were investigated, and the results are summarized in Table 3 and FIG. 10.

TABLE 3

PAA demand/decay (D, k) for 15 wt % and 22 wt % PAA solutions.

| Sample ID | Demand (D, mg/L) | Decay (k, 1/min) |
|---|---|---|
| PAA 15 wt % | 2.81 | 0.125 |
| PAA 22 wt % | 2.55 | 0.096 |

There was minimal difference in the demand/decay kinetics when using either 22% or 15% PAA solutions. There was a slightly higher initial demand and decay using the 15% PAA solution, however the difference was minimal. Both the 22% and 15% PAA solutions displayed the same microbial inactivation kinetics, as microbial inactivation plotted against CT dose show the two inactivation curves essentially overlap.

Four samples collected between September 22-24 were each treated with PAA in order to achieve CT doses ranged from 2.5-50 mg·min/L. The PAA demand/decay results are summarized in Table 4 and FIG. 11. Samples collected in the morning had higher PAA demand (ca. 3.5 mg/L) than samples collected in the afternoon (ca. 2.75 mg/L). This is line with the slightly higher $BOD_5$ measured in those samples. All samples had similar decay rates (ca. 0.060 l/min).

TABLE 4

PAA demand/decay parameters (D, k) for PAA only disinfection.

| Sample ID | Demand (D, mg/L) | Decay (k, 1/min) |
|---|---|---|
| Sept. 22 - AM | 3.58 | 0.063 |
| Sept. 22 - PM | 2.60 | 0.057 |
| Sept. 24 - AM | 3.50 | 0.056 |
| Sept. 24 - PM | 2.91 | 0.058 |

The *E. coli* inactivation kinetics by PAA was calculated for each sample by plotting the viable concentration of *E. coli* on a log scale (y-axis) against the PAA—CT dose (x-axis), and is shown in FIG. 11. Two different models were generated from the data. The first inactivation curve (FIG. 11—top) was generated from the all data collected. This model was used to predict the CT dose required to meet the plant's disinfection target of 63 MPN/100 mL (half the 30-day geomean disinfection permit of 126 MPN/100 mL); CT=49.2 mg·min/L. The second curve (FIG. 11—bottom) was generated using only samples in which the least amount of inactivation was observed per CT dose. In other words, by selecting data corresponding to the maximum MPN at each CT dose applied, a plot of the most challenging inactivation conditions could be generated. This data was then used to estimate the plant's disinfection target of 244 MPN/100 mL (half the daily maximum disinfection permit of 487 MPN/100 mL); CT=36.0 mg·min/L. Based on these results, it is recommended that a PAA CT dose of ≥49.2 mg·min/L be applied in order to meet the plant's disinfection targets.

UV Disinfection Tests

Collimated beam tests were performed to determine the inactivation of *E. coli* by UV irradiation and to determine the UV fluence for sizing a UV system. Over the last 3 years, Trojan Technologies has performed 22 collimated beam tests on multiple samples obtained from the WWTP facility. Water quality ranges from 7-34% UVT and 14-113 mg/L TSS. To provide a robust and representative sizing of the UV disinfection system, all data from the 22 collimated beams tests have been considered in this analysis.

FIG. 13 illustrates data from all the UV collimated beam tests (left) and data representing the poorest inactivation rates (right). Using data in FIG. 13—top, a minimum UV fluence of 20.1 mJ/cm² was required to achieve a target of 63 MPN/100 mL (half the 30-day geomean disinfection permit of 126 MPN/100 mL). The second curve (FIG. 13—bottom) was generated using only samples in which the least amount of inactivation was observed per UV fluence delivered. In other words, the data was segregated by selecting the maximum MPN at each UV fluence applied thereby providing a plot of the most challenging inactivation conditions. This data was then used to calculate that a minimum UV fluence of 19.2 mJ/cm² was required to achieve a target of 244 MPN/100 mL (half the daily maximum disinfection permit of 487 MPN/100 mL).

Combined UV and PAA Disinfection Tests

Three distinct scenarios were performed with respect to testing the combined UV and PAA disinfection processes: UV prior to PAA (UV→PAA), PAA prior to UV (PAA→UV), simultaneous UV and PAA (UV+PAA). For the UV→PAA tests, UV fluences of 10, 15, and 20 mJ/cm² were applied prior to PAA addition, and PAA CTs ranged from 5-25 mg·min/L. Each of FIGS. 14-26 illustrates the results for viable *E. coli* as a function of PAA CT exposure with different levels of UV fluence applied, prior to PAA treatment.

The results of this investigation show clear, consistent, and logical trends:
 (i) for the initial UV treatment, increasing UV fluences treatment resulted in reduced concentration of viable *E. coli*, and
 (ii) for the secondary PAA treatment, increasing PAA CTs resulted in either reduced or constant concentration of viable *E. coli*.

These "trends" are illustrated by the dotted lines in FIGS. 14-16; additionally, this sequence of treatments resulted in both the maximum and geometric mean disinfection targets being met for at least one combination of fluence and CT.

For the PAA→W tests, PAA CTs that ranged from 10-23 mg·min/L were applied prior to UV fluence rates of 10, 15, and 20 mJ/cm². Each of FIGS. 17-19 illustrates the counts of viable *E. coli* as a function of UV fluence with different levels of PAA CT applied prior to UV treatment. The data generally lacks a consistent, logical trend as in some cases there is an increase in viable counts with an increase in treatment level. These "trends" are illustrated by the schematic dotted lines in FIG. 17-19. Further, this sequence of treatments did NOT always result in the geometric mean or maximum disinfection targets being met.

For the simultaneous UV+PAA tests, UV fluence rates of 10, 15, and 20 mJ/cm² were used in conjunction with PAA CTs of 15-30 mg·min/L. Each of FIGS. 20-22 illustrates the results of viable *E. coli* for the simultaneous UV and PAA tests. Data is presented by UV fluence and the respective PAA CT dose applied. In general, the data lacked clear trends; increasing levels of treatments (i.e., higher PAA CTs and UV fluences) did not result in continuously increasing levels of disinfection. Moreover, for reasons not yet evident, the simultaneous treatment scheme could not achieve the geomean or maximum disinfection targets.

Modeling the Sequential UV→PAA

Because the treatment sequence of UV followed by PAA resulted in the most consistent attainment of disinfection targets, this scheme was selected for further analyses including mechanistic modelling and sizing. For the mechanistic modelling, an approach similar to Equation 3 was applied. Equation 3 presents a mechanistic approach where populations of microbes are separated based on their susceptibility to a single disinfectant (UV or PAA) and each population having its own inactivation rate kinetics. For the cases where two disinfectants are applied (UV and PAA) we propose separating the microbes into four populations: ($A_0$) easy to inactivate by UV and PAA, ($B_0$) easy to inactivate by UV, hard to inactivate by PAA, ($C_0$) hard to inactivate by UV, easy to inactivate by PAA, and ($D_0$) hard to inactivate by UV, hard to inactivate by PAA. FIG. 23 provides a conceptual illustration of this mechanistic approach.

Inactivation mechanisms for this system are represented in FIG. 24 and Equation 4 is used to quantify the concentration of viable organisms after disinfection.

$$N_{total,viable(UV_{dose},PAA_{dose})} = A2_{viable} + B2_{viable} + C2_{viable} + D2_{viable} \quad \text{[Equation 4]}$$

where, $N_{total,viable\ (UVdose,PAAdose)}$ is the total concentration of viable *E. coli* remaining after UV and PAA treatment; MPN/100 mL $A2_{viable}$ is the concentration of viable organisms from population $A_0$ remaining after UV and PAA treatment $B2_{viable}$ is the concentration of viable organisms from population $B_0$ remaining after UV and PAA treatment mL $C2_{viable}$ is the concentration of viable organisms from population $C_0$ remaining after UV and PAA treatment mL $D2_{viable}$ is the concentration of viable organisms from population $D_0$ remaining after UV and PAA treatment mL The four population, dual disinfectant model was fitted to the UV only, PAA only, and UV→PAA experimental data to estimate model parameters: $A_0$, $B_0$, $C_0$, $D_0$, $K_{d,UV}$, $K_{d,PAA}$, $K_{p,UV}$, and $K_{p,PAA}$. The resulting model is shown with observed results for UV only and PAA only (FIG. 25) and for UV→PAA (FIG. 26). FIG. 27 provides a comparison between actual results and model predicted concentrations of viable *E. coli*. The four population, dual disinfectant model was able to reasonably predict the effect of UV only, PAA only, and UV→PAA disinfection of *E. coli*.

Summary of Results

The key results that were determined during this study are summarized here:
 There was no observed difference in the inactivation kinetics of 22% and 15% PAA solutions.
 There was no observed difference in the decomposition kinetics of 22% and 15% PAA solutions.
 A PAA CT dose of 49.2 mg·min/L was required to meet the plant's *E. coli* disinfection target of 63 MPN/100 mL.
 A UV fluence of 20.1 mJ/cm² min was required to meet the plant's *E. coli* disinfection target of 63 cfu/100 mL.
 Of the UV and PAA combined treatment schemes, the UV followed by PAA scheme performed the best in that it consistently met disinfection targets.
 A mechanistic model was developed to predict *E. coli* inactivation by the UV only, PAA only, and UV followed by PAA treatment schemes.
 The mechanistic model was used to determine the combination of UV fluence and PAA CT doses required to meet the plant's *E. coli* disinfection target of 63 MPN/100 mL.

The developed correlation can be used to size a combined UV and PAA system as well as perform economic analyses to maximized savings in capital, operating, or net present costs.

CONCLUSIONS

In conclusion, the four population, dual model that was developed with estimated parameters, could be used to size the combination of UV fluences and PAA CT doses that would be required to achieve a 30-day geomean disinfection target of 63 MPN/100 mL at full scale. FIG. 28 (CAPEX=capital expense cost, OPEX=operating expense cost and NPV=net present value) provides a graphical illustration of the combination of disinfectant doses predicted to be required where UV precedes PAA. This plot shows that as the delivered UV fluence is decreased, PAA can be brought online to supplement UV and meet the disinfection target.

It is recommended that this correlation be used to provide disinfection system sizing for a UV+PAA combination system. It is believed that the conceptual evaluation of disinfection economics, including operating and capital costs, for the various UV and PAA combinations be developed to support the disinfection system selection process.

LIST OF REFERENCES

Baldry, M. G. C.; French, M. S.; Slater, D. (1991) The Activity of Peracetic Acid on Sewage Indicator Bacteria and Viruses. Water Science & Technology, 24 (2), 353-357.

Block P and Tran M (2015) Wastewater treatment method. Patent US20150005379.

Bolton J R and Linden K G (2003) Standardization of methods for fluence (UV dose) determination in bench-scale UV experiments. Journal of Environmental Engineering, 129: 209-215.

Budde F E and Vineyard M K (2010) Method of improving efficiency of UV photolysis of peracetic acid for disinfection and organic destruction. Patent US20100176066.

Caretti C and Lubello C (2003) Wastewater disinfection with PAA and UV combined treatment: a pilot plant study. Water Research. 37: 2365-2371.

Gonzalez A, Gehr R, Vaca M, and Lopez R (2012) Disinfection of an advanced primary effluent with peracetic acid and ultraviolet combined treatment: A continuous-flow pilot plant study. Water Environment Research. 84(3): 247-253.

Koivunen J and Heinonen-Tanski H (2005) Inactivation of enteric microorganisms with chemical disinfectants, UV irradiation and combined chemical/UV treatments. Water Research. 39: 1519-1526.

Leaper, S. (1984) Synergistic Killing of Spores of *Bacillus subtilis* by Peracetic Acid and Alcohol. Journal of Food Technology, 19, 355-360.

Lubello C, Gori R, Nicese F P, and Ferrini F (2004) Municipal-treated wastewater reuse for plant nurseries irrigation. Water Research. 38: 2939-2947.

Martin N and Gehr R (2007) Reduction of photoreactivation with the combined UV/peracetic acid process or by delayed exposure to visible light. Water Environment Research. 79(9): 991-999.

Rajala-Mustonen R L, Taviola P S, and Heinonen-Tanksi H (1997) Effects of peracetic acid and UV irradiation on the inactivation of coliphages in wastewater. Water Science & Technology. 35(11-12): 237-241.

Santoro, D., Gehr, R., Bartrand, T. A., Liberti, L, Notarnicola, M., Dell'Erba, A., Falsanisi, D., Haas, C. N. (2007) Wastewater Disinfection by Peracetic Acid: Assessment of Models for Tracking Residual Measurements and Inactivation. Water Environment Research. 79 (7): 775-787.

Santoro, D., Crapulli, F., Raisee, M., Raspa, G., Haas, C. N. (2015) Nondeterministic Computational Fluid Dynamics Modeling of *Escherichia coli* Inactivation by Peracetic Acid in Municipal Wastewater Contact Tanks. Environmental Science & Technology. 49: 7265-7275.

APPENDIX A—TEST PROTOCOL

WWTP Site Test Protocol—UV and PAA Disinfection

Summary

Two (2) secondary effluent samples will be collected daily from the WWTP treated by UV and PAA disinfection. Testing will be conducted over a period of three (3) days during the week of September $21^{st}$. The experiment test matrix described below will be conducted on each of the 6 water samples.

Objective

Evaluate various process design scenarios and operating parameters for a combined UV and PAA disinfection system by running batch disinfection studies under different UV and PAA treatment conditions.

Experiment Test Matrix

These experiments will include variable PAA and UV dosages, alone and in combination. The detailed experimental plan is outlined as:

(a) PAA demand decay test (PAA residuals will be measured at each contact time).

(b) *E. coli* disinfection over a PAA dosage range: 0, 5, 10, 15, 20, and 40 mg/L min.

(c) *E. coli* disinfection over a UV dosage range: 0, 2.5, 5, 10, 20 and 40 $mJ/cm^2$.

(d) *E. coli* disinfection at UV→PAA dosages: Sample pre-treated by UV at 10, 15 and 20 $mJ/cm^2$ dosages followed by PAA dosages of 0, 5, 10, 15, 20 mg/L min.

(e) *E. coli* disinfection at PAA→UV dosages: Sample pre-treated by PAA at CT dose of 5, 10, 15 and 20 mg/L min, followed by irradiation using UV fluences of 0, 10, 15, and 20 $mJ/cm^2$.

(f) *E. coli* disinfection at UV+PAA dosages: Simultaneous addition of PAA and UV at CT doses in the range of 5-10, 10-15, and 15-20 mg/L min and UV doses of 10, 15, and 20 $mJ/cm^2$.

The complete test matrix is shown in Table 1. Two (2) secondary effluent samples will be collected each day for three (3) days. Samples will be collected in attempt to capture average flow and peak flow conditions. For example, the first sample would be collected at 7:00 AM and the second around 1:00 PM. Ten (10) liters of secondary effluent will be collected at each time. Two (2) liters of this sample will be sent to Trojan as a backup. Select experiments will be completed in duplicate.

All the samples will be tested using the same test matrix illustrated in Table 1. UV tests will be conducted using the 50 mL volumes in 60 mL petri dishes. PAA tests will be conducted using appropriate size beakers (500-2000 mL)

TABLE 1

Test matrix for UV/PAA experiments

| Test ID # | Treatment process | UV fluence (mJ/cm$^2$) | PAA CT (mg/L min) | Test Parameters |
|---|---|---|---|---|
| 1 | Control | 0 | 0 | E. coli |
| 2 | PAA alone | 0 | 2.5 | PAA residual, E. coli |
| 3 | PAA alone | 0 | 5 | PAA residual, E. coli |
| 4 | PAA alone | 0 | 10 | PAA residual, E. coli |
| 5 | PAA alone | 0 | 15 | PAA residual, E. coli |
| 6 | PAA Alone | 0 | 20 | PAA Residual, E. coli |
| 7 | PAA Alone | 0 | 40 | PAA Residual, E. coli |
| 8 | UV alone | 2.5 | 0 | E. coli |
| 9 | UV alone | 5 | 0 | E. coli |
| 10 | UV alone | 10 | 0 | E. coli |
| 11 | UV alone | 15 | 0 | E. coli |
| 12 | UV Alone | 20 | 0 | E. coli |
| 13 | UV Alone | 40 | 0 | E. coli |
| 14 | UV + PAA | 10 | 5 | PAA residual, E. coli |
| 15 | UV + PAA | 10 | 10 | PAA residual, E. coli |
| 16 | UV + PAA | 10 | 15 | PAA residual E. coli |
| 17 | UV + PAA | 10 | 20 | PAA residual, E. coli |
| 18 | UV + PAA | 15 | 5 | PAA residual, E. coli |
| 19 | UV + PAA | 15 | 10 | PAA residual, E. coli |
| 20 | UV + PAA | 15 | 15 | PAA residual E. coli |
| 21 | UV + PAA | 15 | 20 | PAA residual, E. coli |
| 22 | UV + PAA | 20 | 5 | PAA residual, E. coli |
| 23 | UV + PAA | 20 | 10 | PAA residual, E. coli |
| 24 | UV + PAA | 20 | 15 | PAA residual, E. coli |
| 25 | UV + PAA | 20 | 20 | PAA residual, E. coli |
| 26 | PAA + UV | 10 | 5 | PAA residual, E. coli |
| 27 | PAA + UV | 15 | 5 | PAA residual, E. coli |
| 28 | PAA + UV | 20 | 5 | PAA residual, E. coli |
| 29 | PAA + UV | 10 | 10 | PAA residual, E. coli |
| 30 | PAA + UV | 15 | 10 | PAA residual, E. coli |
| 31 | PAA + UV | 20 | 10 | PAA residual, E. coli |
| 32 | PAA + UV | 10 | 15 | PAA residual, E. coli |
| 33 | PAA + UV | 15 | 15 | PAA residual, E. coli |
| 34 | PAA + UV | 20 | 15 | PAA residual, E. coli |
| 35 | PAA + UV | 10 | 20 | PAA residual, E. coli |
| 36 | PAA + UV | 15 | 20 | PAA residual, E. coli |
| 37 | PAA + UV | 20 | 20 | PAA residual, E. coli |
| 38 | Simult. PAA + UV | 10 | 5-10 | PAA residual, E. coli |
| 39 | Simult. PAA + UV | 10 | 5-10 | PAA residual, E. coli |
| 40 | Simult. PAA + UV | 10 | 10-15 | PAA residual, E. coli |
| 41 | Simult. PAA + UV | 10 | 15-20 | PAA residual, E. coli |
| 42 | Simult. PAA + UV | 15 | 10-15 | PAA residual, E. coli |
| 43 | Simult. PAA + UV | 15 | 10-15 | PAA residual, E. coli |
| 44 | Simult. PAA + UV | 15 | 15-20 | PAA residual, E. coli |
| 45 | Simult. PAA + UV | 20 | 15-20 | PAA residual, E. coli |
| 46 | Simult. PAA + UV | 20 | 15-20 | PAA residual, E. coli |
| 47 | Simult. PAA + UV | 10 | 5-10 | PAA residual, E. coli |
| 48 | Simult. PAA + UV | 10 | 10-15 | PAA residual, E. coli |
| 49 | Simult. PAA + UV | 10 | 15-20 | PAA residual, E. coli |
| 50 | Simult. PAA + UV | 15 | 10-15 | PAA residual, E. coli |
| 51 | Simult. PAA + UV | 15 | 15-20 | PAA residual, E. coli |
| 52 | Simult. PAA + UV | 20 | 15-20 | PAA residual, E. coli |

The total number of tests per sample is shown in Table 2.

TABLE 2

Total numbers of samples and volume

| Test | Microbe | PAA | Volume (mL) |
|---|---|---|---|
| Demand &Decay | 0 | 5 | 500 |
| Controls/Calibration | 12 | 6 | 600 |
| PAA alone/PAA + UV | 50 | 6 | 1500 |
| UV alone/UV + PAA | 46 | 12 | 1200 |
| Simult. PAA + UV | 36 | 15 | 750 |
| Total number of samples or volume | 144 | 44 | 4550 |

Methods

Analytical Methods

UV collimated beam and PAA measurements will be conducted following the established SOPs developed by Trojan Technologies.

E. coli measurements will be performed by a laboratory following the Idexx Colisure protocol.

Color and UVT will be measured on-site by CDM. TSS, COD, and BOD will be measured by an external lab, arranged by CDM.

UV irradiation times and PAA contact times provided in the test plan below are estimates based on previous experiments performed by Trojan Technologies on WWTP secondary effluent samples. The actual UV irradiation and PAA contact times to be used will be determined for each collected sample prior to analysis.

Test Procedures

1. Prepare PAA stock solution (1000 mg/L) from 22% PAA, measure the concentration using titration method (see SOP—PAA production and testing) and with CHEMetrics test kit.
2. Prepare a second PAA stock solution (10,000 mg/L) from 22% PAA, and measure the concentration using titration method (see SOP—PAA production and testing) and with CHEMetrics test kit.
3. Prepare sodium bisulfite stock solution (0.01M) from commercial standard.
4. Collect 6×100 mL of sample and set aside as controls for E. coli analysis.
   4.1. Suggested dilutions are: 4 log, 3 log.
5. Conduct PAA demand/decay pre-test.
   5.1 Measure 250 mL of sample and pour into 500 mL beaker.
   5.2 Add appropriate volume of PAA stock solution (1000 mg/L) to obtain 4 mg/L PAA in the 250 mL sample. Start timer immediately after addition. The stir rate for PAA reaction is level 10.
   5.3 Measure residual PAA (by removing 25 mL and adding to CHEMetrics test kit) at time intervals of:
      5.3.1 0.5 min
      5.3.2 2 min
      5.3.3 4 min
      5.3.4 8 min
      5.3.5 16 min
   5.4 Quench sample with 0.01 M NaHSO$_3$ stock solution (stoichiometric) and discard.
   5.5 Measure background PAA reading for the water sample, in triplicate.
   5.6 Record actual concentration of PAA added to sample by dosing in the same volume of PAA stock solution into 250 mL DI water, in triplicate.
   5.7 Record measured PAA residuals in the file "Decay Demand Analysis for CT Estimates".
   5.8 Repeat steps 5.1-5.7 one more time on the same water sample.
   5.9 Repeat steps 5.1-5.7 with PAA stock solution (10,000 mg/L)
6. Conduct PAA/PAA+UV test:
   6.1 Measure 1500 mL of sample and pour into 2000 mL beaker.
   6.2 Target a PAA residual of approximately 2 mg/L after 30 seconds, based on step 3, calculate the time required to achieve the above CT (to be estimated with a preliminary decay test), keeping in mind that the actual CT would need to be recalculated for the actual residual PAA concentration measured during PAA disinfection experiments.

6.3 Add PAA concentration calculated from step 5.2, start timer immediately after addition.

6.4 Measure residual PAA (by removing 25 mL and adding to CHEMetrics test kit) at required CT (approx. 1:01, 2:05, 4:19, 6:44, 9:21 and 23:01 min:sec)

6.5 At the following times, the designated volume of sample is withdrawn and a stoichiometric amount of sodium bisulfate stock solution is added to quench the residual (to ensure immediate quenching at the required time).

6.5.1 For time 1:01, collect 100 mL of sample for microbial testing 6.5.2 For times 2:05-9:21, collect 300 mL of sample for microbial testing and to be used for PAA+UV testing 6.5.3 For time 23:01, collect 100 mL of sample for microbial testing 6.6 For each 300 mL subsample collected for PAA+UV analysis (times 2:05-9:21), subsample 50 mL for microbial testing. Use the remaining 250 mL to prepare 50 mL samples for UV irradiation.

6.6.1 Measure the UV intensity of the collimated beam to use in calculating the irradiation time (based on the spreadsheet developed by Trojan Technologies—see SOP-collimated beam). The stir rate for UV collimated beam should be set at level 10.

6.6.2 Irradiate 50 mL volume from the subsample to a fluence of 10 mJ/cm$^2$. Retain the 50 mL of sample for *E. coli* analysis.

6.6.3 To a new 50 mL sample, irradiate to a fluence of 15 mJ/cm$^2$. Retain the 50 mL of sample for *E. coli* analysis.

6.6.4 To a new 50 mL sample, irradiate to a fluence of 20 mJ/cm$^2$. Retain the 50 mL of sample for *E. coli* analysis.

6.6.5 Repeat 6.6.1-6.6.4 for each 300 mL subsample.

TABLE 3

Sample dilutions for *E. coli* enumeration

| Test ID # | UV Fluence (mJ/cm$^2$) | PAA CT (mg/L min) | Dilution |
|---|---|---|---|
| 2 | 0 | 2.5 | 4 log, 3 log |
| 3 | 0 | 5 | 3 log, 2 log |
| 26 | 10 | 5 | 2 log, 1 log |
| 27 | 15 | 5 | 1 log, none |
| 28 | 20 | 5 | none |
| 4 | 0 | 10 | 2 log, 1 log |
| 29 | 10 | 10 | 1 log, none |
| 30 | 15 | 10 | none |
| 31 | 20 | 10 | none |
| 5 | 0 | 15 | 1 log, none |
| 32 | 10 | 15 | none |
| 33 | 15 | 15 | none |
| 34 | 20 | 15 | none |
| 6 | 0 | 20 | none |
| 35 | 10 | 20 | none |
| 36 | 15 | 20 | none |
| 37 | 20 | 20 | none |
| 7 | 0 | 40 | none |

7. Conduct UV+PAA test:

7.1 Measure the UV intensity of the collimated beam to use in calculating the irradiation time (based on the spreadsheet developed by Trojan Technologies—see SOP-collimated beam). The stir rate for UV collimated beam should be set at level 10.

7.2 Irradiate 50 mL volume at the specified fluence, ex. 10 mJ/cm$^2$, 7.3 Repeat step 7.2 six more times to obtain 350 mL of irradiated sample.

7.4 Withdraw 50 mL of sample for *E. coli* analysis.

7.5 Spike the leftover UV irradiated composite batch with PAA to obtain a 2 mg/L residual (after 30 seconds), and start timer.

7.6 Withdraw samples: 25 mL for PAA analysis and 50 mL for *E. coli* (to be quenched with NaHSO$_3$) at 2:05, 4:19, 6:44 and 9:21 min:sec.

7.7 Repeat steps 7.5-7.6 for remaining UV intensities (15 and 20 mJ/cm$^2$)

TABLE 4

Suggested dilutions for *E. coli* coliform enumeration

| Test ID # | UV Fluence (mJ/cm$^2$) | PAA CT (mg/L min) | Dilutions |
|---|---|---|---|
| 10 | 10 | 0 | 2 log, 1 log |
| 14 | 10 | 5 | 1 log, none |
| 15 | 10 | 10 | none |
| 16 | 10 | 15 | none |
| 17 | 10 | 20 | none |
| 11 | 15 | 0 | 1 log, none |
| 18 | 15 | 5 | none |
| 19 | 15 | 10 | none |
| 20 | 15 | 15 | none |
| 21 | 15 | 20 | none |
| 12 | 20 | 0 | none |
| 22 | 20 | 5 | none |
| 23 | 20 | 10 | none |
| 24 | 20 | 15 | none |
| 25 | 20 | 20 | none |

8. Conduct UV alone test:

8.1 Repeat step 7.1 to determine the irradiation time required for each target UV dosage (2.5, 5, 40 mJ/cm$^2$).

8.2 Use 50 mL secondary effluent samples and irradiate using the calculated durations from step 6.1

8.3 Retain the entire 50 mL of sample for *E. coli* analysis.

8.3 Repeat steps 8.1-8.3 for remaining UV fluences.

TABLE 5

Suggested sample dilutions for *E. coli* enumeration

| Test ID # | UV Fluence (mJ/cm$^2$) | Dilutions |
|---|---|---|
| 8 | 2.5 | 4 log, 3 log |
| 9 | 5 | 3 log, 2 log |
| 13 | 40 | none |

9. Conduct simultaneous UV+PAA:

9.1. A detailed test matrix for this section is provided as an appendix.

9.2. Place 50 mL sample under UV lamp while simultaneously adding PAA (spike to 2 mg/L after residual, as calculated previously)

9.3. Irradiate sample for 3:32 (ca. 10 mJ/cm$^2$). Remove sample from UV, remove 10 mL for PAA analysis, and quench remaining sample with NaHSO$_3$. Use 10 mL sub-sample to measure PAA residual concentration. Use the remaining 40 mL of sample for *E. coli* analysis.

9.4. For a new sample, irradiate for 3:32 (ca. 10 mJ/cm$^2$), while simultaneously adding PAA (spike to 2 mg/L after residual, as calculated previously). Remove sample and let stir additional 0:47, remove 10 mL for PAA analysis, and quench remaining sample with NaHSO$_3$. Use the remaining 40 mL of sample for *E. coli* analysis.

9.5. For a new sample, irradiate for 3:32 (ca. 10 mJ/cm$^2$), while simultaneously adding PAA (spike to 2 mg/L after residual, as calculated previously). Remove sample and let stir additional 3:12, remove 10 mL for PAA analysis, and quench remaining sample with NaHSO$_3$. Use the remaining 40 mL of sample for *E. coli* analysis.

9.6. For a new sample, irradiate for 3:32 (ca. 10 mJ/cm$^2$), while simultaneously adding PAA (spike to 2 mg/L after residual, as calculated previously). Remove sample and let stir additional 5:49, remove 10 mL for PAA analysis, and quench remaining sample with NaHSO$_3$. Use the remaining 40 mL of sample for *E. coli* analysis.

9.7. For a new sample, irradiate for 5:18 (ca. 15 mJ/cm$^2$), while simultaneously adding PAA (spike to 2 mg/L after residual, as calculated previously). Remove sample from UV, and remove 10 mL for PAA analysis, and quench remaining sample with NaHSO$_3$. Use the remaining 40 mL of sample for *E. coli* analysis.

9.8. For a new sample, irradiate for 5:18 (ca. 15 mJ/cm$^2$), while simultaneously adding PAA (spike to 2 mg/L after residual, as calculated previously). Remove sample and let stir additional 1:26, remove 10 mL for PAA analysis, and quench remaining sample with NaHSO$_3$. Use the remaining 40 mL of sample for *E. coli* analysis.

9.9. For a new sample, irradiate for 5:18 (ca. 15 mJ/cm$^2$), while simultaneously adding PAA (spike to 2 mg/L after residual, as calculated previously). Remove sample and let stir additional 4:03, remove 10 mL for PAA analysis, and quench remaining sample with NaHSO$_3$. Use the remaining 40 mL of sample for *E. coli* analysis.

9.10. For a new sample, irradiate for 7:05 (ca. 20 mJ/cm$^2$), while simultaneously adding PAA (spike to 2 mg/L after residual, as calculated previously). Remove sample from UV, and remove 10 mL for PAA analysis, and quench remaining sample with NaHSO$_3$. Use the remaining 40 mL of sample for *E. coli* analysis.

9.11. For a new sample, irradiate for 7:05 (ca. 20 mJ/cm$^2$), while simultaneously adding PAA (spike to 2 mg/L after residual, as calculated previously). Remove sample and let stir additional 2:17, remove 10 mL for PAA analysis, and quench remaining sample with NaHSO$_3$. Use the remaining 40 mL of sample for *E. coli* analysis.

10. Conduct simultaneous PAA+UV:
    10.1. A detailed test matrix for this section is provided as an appendix.
    10.2. Place 50 mL sample on stir plate and add PAA (spike to 2 mg/L after residual, as calculated previously) Stir sample for 0:47 and then place under UV lamp. Stir for additional 3:32 (ca. 10 mJ/cm$^2$) and then remove from lamp. Remove 10 mL for PAA analysis, and quench remaining sample with NaHSO$_3$. Use the remaining 40 mL of sample for *E. coli* analysis.
    10.3. For a new sample, place 50 mL sample on stir plate and add PAA (spike to 2 mg/L after residual, as calculated previously) Stir sample for 3:12 and then place under UV lamp. Stir for additional 3:32 (ca. 10 mJ/cm$^2$) and then remove from lamp. Remove 10 mL for PAA analysis, and quench remaining sample with NaHSO$_3$. Use the remaining 40 mL of sample for *E. coli* analysis.
    10.4. For a new sample, place 50 mL sample on stir plate and add PAA (spike to 2 mg/L after residual, as calculated previously) Stir sample for 5:49 and then place under UV lamp. Stir for additional 3:32 (ca. 10 mJ/cm$^2$) and then remove from lamp. Remove 10 mL for PAA analysis, and quench remaining sample with NaHSO$_3$. Use the remaining 40 mL of sample for *E. coli* analysis.
    10.5. For a new sample, place 50 mL sample on stir plate and add PAA (spike to 2 mg/L after residual, as calculated previously) Stir sample for 1:26 and then place under UV lamp. Stir for additional 5:18 (ca. 15 mJ/cm$^2$) and then remove from lamp. Remove 10 mL for PAA analysis, and quench remaining sample with NaHSO$_3$. Use the remaining 40 mL of sample for *E. coli* analysis.
    10.6. For a new sample, place 50 mL sample on stir plate and add PAA (spike to 2 mg/L after residual, as calculated previously) Stir sample for 4:03 and then place under UV lamp. Stir for additional 5:18 (ca. 15 mJ/cm$^2$) and then remove from lamp. Remove 10 mL for PAA analysis, and quench remaining sample with NaHSO$_3$. Use the remaining 40 mL of sample for *E. coli* analysis.
    10.7. For a new sample, place 50 mL sample on stir plate and add PAA (spike to 2 mg/L after residual, as calculated previously) Stir sample for 2:17 and then place under UV lamp. Stir for additional 7:04 (ca. 20 mJ/cm$^2$) and then remove from lamp. Remove 10 mL for PAA analysis, and quench remaining sample with NaHSO$_3$. Use the remaining 40 mL of sample for *E. coli* analysis.

TABLE 6

Suggested sample dilutions for *E. coli* enumeration

| Test ID # | UV Fluence (mJ/cm$^2$) before PAA | PAA CT (mg/L min) | UV Fluence (mJ/cm$^2$) after PAA | Dilutions |
|---|---|---|---|---|
| 38 | 10 | 5-10 | — | 1 log, none |
| 39 | 10 | 5-10 | — | 1 log, none |
| 40 | 10 | 10-15 | — | none |
| 41 | 10 | 15-20 | — | none |
| 42 | 15 | 10-15 | — | none |
| 43 | 15 | 10-15 | — | none |
| 44 | 15 | 15-20 | — | none |
| 45 | 20 | 15-20 | — | none |
| 46 | 20 | 15-20 | — | none |
| 47 | — | 5-10 | 10 | 1 log, none |
| 48 | — | 10-15 | 10 | none |
| 49 | — | 15-20 | 10 | none |
| 50 | — | 10-15 | 15 | none |
| 51 | — | 15-20 | 15 | none |
| 52 | — | 15-20 | 20 | none |

Material
  Collimated beam, Extra lamp for collimated beam, radiometer
  CHEMetrics PAA analyzer
  PAA test kits
  Sample vials for microbial analysis
  UVT detector
  PAA stock solution, provided on site
  Sodium sulfite for quenching
  wash bottle
  Sample bottles for collecting samples Cooler for transporting samples
micropipettes, 0.1-1 mL, 10-100 μL.
pipette tips
autopipetter, plus larger pipettes (10-50 mL)
grad cylinders, 1×50 mL, 1×500 mL
60 mL petri dishes with stir bars
500 mL beakers, 2000 mL beakers
stop watch/timer
stir plates
Kim wipes
labels, markers, tape, pens, etc
small, brown glass sample bottles to prepare stock solutions of PAA and quench NaHSO3
Cerium Sulfate
sodium thiosulfate
hach sulfate 1 test packetes
ferroin indicator
burret for PAA titration
50 mL Erlenmeyer flasks

APPENDIX: TEST MATRIX FOR
SIMULTANEOUS UV+PAA AND PAA+UV

| Test ID # | Treatment process | UV irradiation time (min) | UV Dosage (mJ/cm$^2$) | Additional PAA contact time (min) | Total Contact time (min) | Total PAA CT (mg/L min) |
|---|---|---|---|---|---|---|
| 38 | Simult. UV + PAA | 3:32 | 10 | 0 | 3:32 | between 5-10 |
| 39 | Simult. UV + PAA | 3:32 | 10 | 0:47 | 4:19 | between 5-10 |
| 40 | Simult. UV + PAA | 3:32 | 10 | 3:12 | 6:44 | between 10-15 |
| 41 | Simult. UV + PAA | 3:32 | 10 | 5:49 | 9:21 | between 15-20 |
| 42 | Simult. UV + PAA | 5:18 | 15 | 0 | 5:18 | between 10-15 |
| 43 | Simult. UV + PAA | 5:18 | 15 | 1:26 | 6:44 | between 10-15 |
| 44 | Simult. UV + PAA | 5:18 | 15 | 4:03 | 9:21 | between 15-20 |
| 45 | Simult. UV + PAA | 7:04 | 20 | 0 | 7:04 | between 15-20 |
| 46 | Simult. UV + PAA | 7:04 | 20 | 2:17 | 9:21 | between 15-20 |
| 47 | Simult. PAA + UV | 0:47 | 3:32 | 10 | 4:19 | between 5-10 |
| 48 | Simult. PAA + UV | 3:12 | 3:32 | 10 | 6:44 | between 10-15 |
| 49 | Simult. PAA + UV | 5:49 | 3:32 | 10 | 9:21 | between 15-20 |
| 50 | Simult. PAA + UV | 1:26 | 5:18 | 15 | 6:44 | between 10-15 |
| 51 | Simult. PAA + UV | 4:03 | 5:18 | 15 | 9:21 | between 15-20 |
| 52 | Simult. PAA + UV | 2:17 | 7:04 | 20 | 9:21 | between 15-20 |

While this invention has been described with reference to illustrative embodiments and examples, the description is not intended to be construed in a limiting sense. Thus, various modifications of the illustrative embodiments, as well as other embodiments of the invention, will be apparent to persons skilled in the art upon reference to this description. It is therefore contemplated that the appended claims will cover any such modifications or embodiments.

All publications, patents and patent applications referred to herein are incorporated by reference in their entirety to the same extent as if each individual publication, patent or patent application was specifically and individually indicated to be incorporated by reference in its entirety.

What is claimed is:

1. An on-line device for controlling a fluid treatment process configured to inactivate a microorganism in a flow of fluid using ultraviolet radiation and a chemical disinfectant, the device comprising:
    a memory for receiving a calculated database of dose response for the ultraviolet radiation and for the chemical disinfectant for a fluid treatment parameter, wherein the memory stores code, the code executable by a processor to:
    obtain input data about the fluid treatment parameter from the process;
    compare the input data with the calculated database;
    receive a treatment constraint, wherein the treatment constraint is based on a multi-target disinfection to determine an optimal sequence for the chemical disinfectant, wherein the multi-target disinfection comprises a plurality of disinfectants, wherein the treatment constraint is based at least upon a disinfection kinetic of each disinfectant; and
    adjust one or more of an amount of ultraviolet radiation and the chemical disinfectant added to the flow fluid in response to a difference between the input data, the calculated database, and the treatment constraint.

2. The device defined in claim 1, wherein the chemical disinfectant is selected from the group consisting of a peracid and peracetic acid (PAA).

3. The device defined in claim 1, wherein the fluid treatment parameter is selected from the group consisting of an operating cost to treat the flow of fluid, the cost of ultraviolet radiation to treat the flow of fluid, a cost of the chemical disinfectant to treat the flow of fluid, a cost of the ultraviolet radiation and the chemical disinfectant to treat the flow of fluid, a cost of electricity to treat the flow of fluid, and a daily volume fluid treated by the fluid treatment parameter.

4. The device defined in claim 1, wherein the calculated database is based on empirical data obtained from a chemical disinfectant dose response curve for the fluid treatment parameter.

5. The device defined in claim 1, wherein the fluid treatment process is configured to inactivate the microorganism in the flow of fluid using ultraviolet radiation and the chemical disinfectant concurrently.

6. The device defined in claim 1, wherein the fluid treatment process is configured to inactivate the microorganism in the flow of fluid using ultraviolet radiation and the chemical disinfectant sequentially.

7. The device defined in claim 1, wherein the fluid treatment process is configured to inactivate the microorganism in the flow of fluid using ultraviolet radiation prior to the chemical disinfectant.

8. The device defined in claim 1, wherein the fluid treatment process is configured to inactivate the microorganism in the flow of fluid using ultraviolet radiation after the chemical disinfectant.

9. A process for controlling a fluid treatment process configured to inactivate a microorganism in a flow of fluid using ultraviolet radiation and a chemical disinfectant, the process comprising the steps of:
    obtaining input data about a fluid treatment parameter;
    comparing the input data with a calculated database of dose response for the ultraviolet radiation and for the chemical disinfectant for the fluid treatment parameter;

receiving a treatment constraint, wherein the treatment constraint is based on a multi-target disinfection to determine an optimal sequence of the chemical disinfectant, wherein the multi-target disinfection comprises a plurality of disinfectants, wherein the treatment constraint is based at least upon a disinfection kinetic of each disinfectant; and adjusting one or more of an amount ultraviolet radiation and the chemical disinfectant added to the flow fluid in response to a difference between the input data, the calculated database, and the treatment constraint.

10. The process defined in claim 9, wherein the chemical disinfectant is selected from the group consisting of a peracid and peracetic acid (PAA).

11. The process defined in claim 9, wherein the fluid treatment parameter is selected from the group consisting of an operating cost to treat the flow of flow, a cost of ultraviolet radiation to treat the flow of fluid, a cost of the chemical disinfectant to treat the flow of fluid, a cost of the ultraviolet radiation and the chemical disinfectant to treat the flow of fluid, a cost of electricity to treat the flow of fluid, and a daily volume fluid treated by the fluid treatment parameter.

12. The process defined in claim 9, wherein the calculated database is based on empirical data obtained from a chemical disinfectant dose response curve for the fluid treatment parameter.

13. The process defined in claim 9, wherein the fluid treatment process is configured to inactivate the microorganism in the flow of fluid using ultraviolet radiation and the chemical disinfectant concurrently.

14. The process defined in claim 9, wherein the fluid treatment process is configured to inactivate the microorganism in the flow of fluid using ultraviolet radiation and the chemical disinfectant sequentially.

15. The process defined in claim 9, wherein the fluid treatment process is configured to inactivate the microorganism in the flow of fluid using ultraviolet radiation prior to the chemical disinfectant.

16. The process defined in claim 9, wherein the fluid treatment process is configured to inactivate the microorganism in the flow of fluid using ultraviolet radiation after the chemical disinfectant.

* * * * *